United States Patent
Chen et al.

(10) Patent No.: US 8,639,310 B2
(45) Date of Patent: Jan. 28, 2014

(54) SYSTEM AND METHODS FOR LOCATING AND ABLATING ARRHYTHOMOGENIC TISSUES

(71) Applicants: Peter C. Chen, Irvine, CA (US); Alan de la Rama, Cerritos, CA (US); Cary K. Hata, Irvine, CA (US); Vivian Tran, Laguna Niguel, CA (US)

(72) Inventors: Peter C. Chen, Irvine, CA (US); Alan de la Rama, Cerritos, CA (US); Cary K. Hata, Irvine, CA (US); Vivian Tran, Laguna Niguel, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 13/778,900

(22) Filed: Feb. 27, 2013

(65) Prior Publication Data
US 2013/0237791 A1    Sep. 12, 2013

Related U.S. Application Data

(60) Continuation of application No. 13/090,832, filed on Apr. 20, 2011, now abandoned, which is a division of application No. 11/583,263, filed on Oct. 19, 2006, now abandoned, which is a continuation-in-part of application No. 10/897,887, filed on Jul. 22, 2004, now abandoned, which is a continuation-in-part of application No. 10/744,354, filed on Dec. 22, 2003, now abandoned, which is a continuation of application No. 09/975,269, filed on Oct. 11, 2001, now Pat. No. 6,671,533.

(51) Int. Cl.
*A61B 5/04*  (2006.01)
*A61B 18/04* (2006.01)
*A61B 18/14* (2006.01)

(52) U.S. Cl.
USPC ............ 600/374; 600/381; 606/27; 606/41

(58) Field of Classification Search
USPC ..................... 600/374, 381; 606/27, 41
See application file for complete search history.

(56) References Cited

U.S. PATENT DOCUMENTS

| | | | |
|---|---|---|---|
| 5,582,609 A | | 12/1996 | Swanson et al. |
| 5,782,828 A | | 7/1998 | Chen et al. |
| 5,897,554 A | | 4/1999 | Chia et al. |
| 6,529,756 B1 | * | 3/2003 | Phan et al. ............. 600/374 |
| 6,652,517 B1 | * | 11/2003 | Hall et al. ................ 606/41 |
| 6,771,996 B2 | * | 8/2004 | Bowe et al. ............. 600/374 |
| 7,410,486 B2 | * | 8/2008 | Fuimaono et al. ......... 606/41 |
| 2005/0010095 A1 | * | 1/2005 | Stewart et al. .......... 600/374 |
| 2005/0165388 A1 | * | 7/2005 | Bhola ..................... 606/14 |
| 2005/0256518 A1 | | 11/2005 | de la Rama et al. |

FOREIGN PATENT DOCUMENTS

| | | |
|---|---|---|
| EP | 0911059 | 4/1999 |
| EP | 1042990 | 10/2000 |
| WO | 9513111 | 5/1995 |

* cited by examiner

Primary Examiner — Lee S Cohen
(74) Attorney, Agent, or Firm — Wiley Rein LLP

(57) ABSTRACT

The disclosure relates to a variety of systems and methods for sensing electrical events about a selected annulus region of the heart and for treating tissue in the selected annulus region. Wherein the system includes a first catheter that has an expandable member, an ablation element, and a lumen configured to allow a second catheter therethrough. The second catheter includes a distal section in a ring shape and a plurality of electrodes coupled around the ring. Optionally a second lumen can be included through the first catheter that allows for contrast media to be delivered to the distal end of the system.

13 Claims, 32 Drawing Sheets

SECTION A-A

SECTION B-B

SECTION A-A

SECTION B-B

SECTION A-A

SECTION B-B

SECTION A-A

SYSTEM AND METHODS FOR LOCATING AND ABLATING ARRHYTHOMOGENIC TISSUES

CROSS-REFERENCE TO RELATED APPLICATIONS

This application is a continuation of U.S. application Ser. No. 13/090,832, filed 20 Apr. 2011 (the '832 application), now abandoned, which is a divisional of U.S. application Ser. No. 11/583,263, filed 19 Oct. 2006 (the '263 application), now abandoned, which is a continuation-in-part of U.S. application Ser. No. 10/897,887, filed 22 Jul. 2004 (the '887 application), now abandoned, which is in turn a continuation-in-part of U.S. application Ser. No. 10/744,354, filed 22 Dec. 2003 (the '354 application), now abandoned, which is in turn a continuation of U.S. application Ser. No. 09/975,269, filed 11 Oct. 2001 (the '269 application), now U.S. Pat. No. 6,671,533. The '832 application, the '263 application, the '887 application, the '354 application, and the '269 application are hereby incorporated by reference in their entirety as though fully set forth herein.

BACKGROUND OF THE INVENTION a. Field of the Invention

The present invention is directed to systems and methods for mapping and ablating body tissue of the interior regions of the heart for treating cardiac arrhythmias.

b. Description of the Prior Art

Atrial fibrillation (AF) is a common cardiac arrhythmia associated with significant morbidity and mortality. A number of clinical conditions may arise from irregular cardiac functions and the resulting hemodynamic abnormalities associated with AF, including stroke, heart failure and other thromboembolic events. AF is a significant cause of cerebral stroke, wherein the fibrillating motion in the left atrium induces the formation of thrombus. A thromboembolism is subsequently dislodged into the left ventricle and enters the cerebral circulation where stroke may result.

For many years, the only curative treatment for AF has been surgical, with extensive atrial incisions used to compartmentalize the atrial mass below that critical for perpetuating AF. Recently, transcatheter linear radiofrequency ablation in the right or left atrium has been used to replicate surgical procedures in patients with paroxysmal or chronic AF. Such ablation is carried out by a catheter system that performs both mapping and ablation. With current techniques, there is still uncertainty regarding the number of lesions, the optimum ablation site, and the need for continuous lines. As a result, focal ablation has been proposed as an alternative approach, due to the belief that ectopic beats originating within or at the ostium of the pulmonary veins (PV) may be the source of paroxysmal and even persistent AF. Although successful, the technical feasibility of this technique is restricted by the difficulty in mapping the focus if the patient is in AF or has no consistent firing, the frequent existence of multiple foci causing high recurrence rates, and a high incidence of PV stenosis.

There are a number of drawbacks associated with the catheter-based mapping and ablation systems that are currently known in the art. One serious drawback lies in the unstable positioning of the catheter inside the atrium of the heart. When a catheter is not properly stabilized, the mapping becomes difficult and inaccurate.

Another drawback is associated with certain catheter-based systems that utilize an expandable balloon that is inflated to conform to the pulmonary vein ostium. After the balloon is inflated and the catheter positioned, it becomes difficult to map or record the distal PV potentials without removing this catheter and placing another mapping catheter inside the PV. Moreover, inflation of the balloon to conform to the pulmonary vein ostium blocks blood flow to the left atrium, and such prolonged blockage can have adverse effects to the patient. Blockage of blood flow from the PV deprives the patient from receiving oxygenated blood. In addition, the blockage may be a potential source for stenosis.

Thus, there still remains a need for a catheter-based system and method that can effectively map and ablate potentials (also known as spikes) inside PVs which can induce paroxysmal AF, while avoiding the drawbacks set forth above.

BRIEF SUMMARY OF THE DISCLOSURE

It is an objective of the present invention to provide a system and method that effectively maps or records distal PV potentials and ablates the PV ostium.

It is another objective of the present invention to provide a system and method that effectively maps and ablates potentials without blocking blood flow.

In order to accomplish the objects of the present invention, there is provided a catheter for sensing electrical events about a selected annulus region of the heart and for treating tissue in the selected annulus region. The catheter has a handle assembly, a shaft having a proximal end coupled to the handle assembly, a first expandable member provided at the distal end of the shaft, and a second expandable member positioned adjacent to, but spaced apart from, the first expandable member. The second expandable member has an ablation element that emits energy to a radially surrounding area to ablate tissue.

DETAILED DESCRIPTION OF EMBODIMENTS OF THE INVENTION

Figure 1:
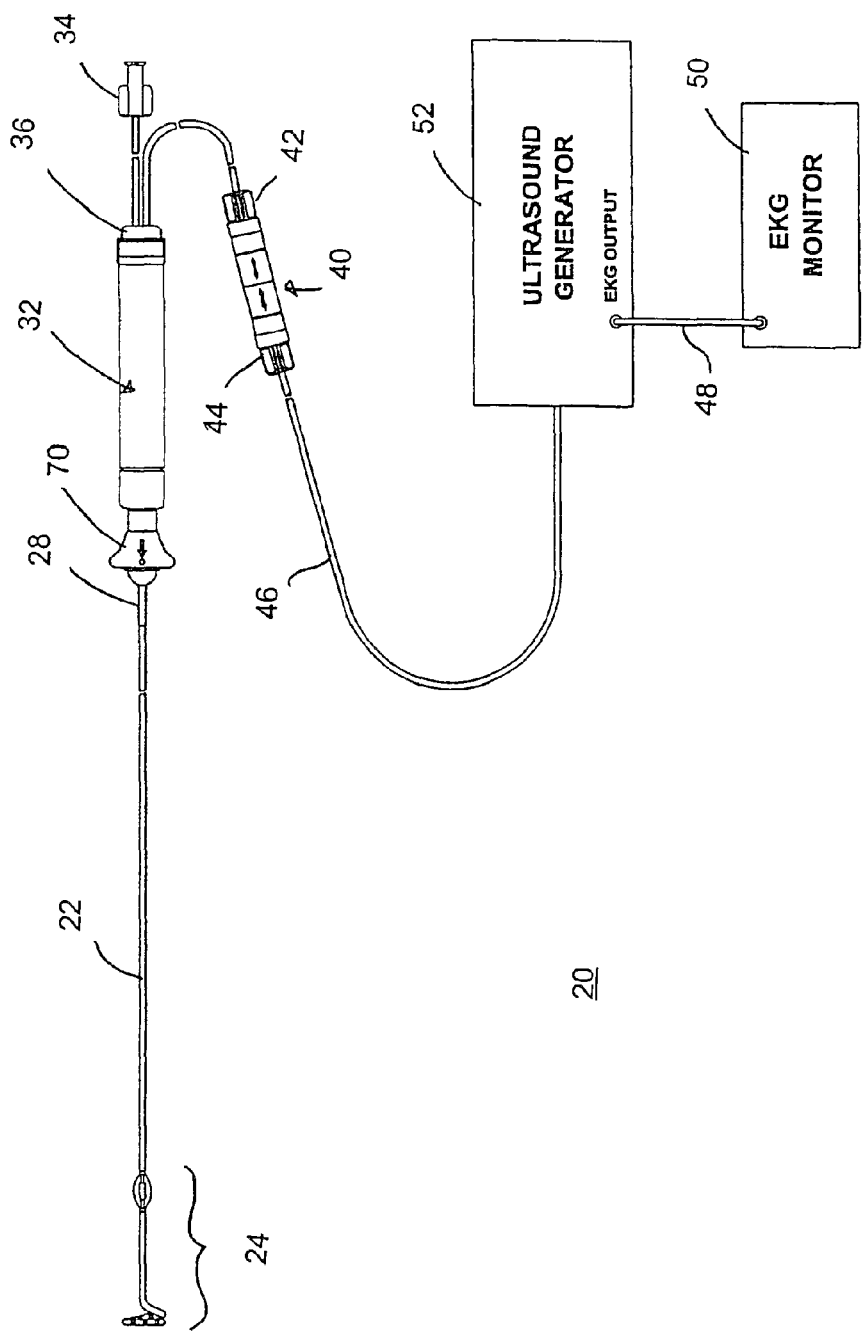
FIG. 1 illustrates a mapping and ablation system according to one embodiment of the present invention.
Figure 2:
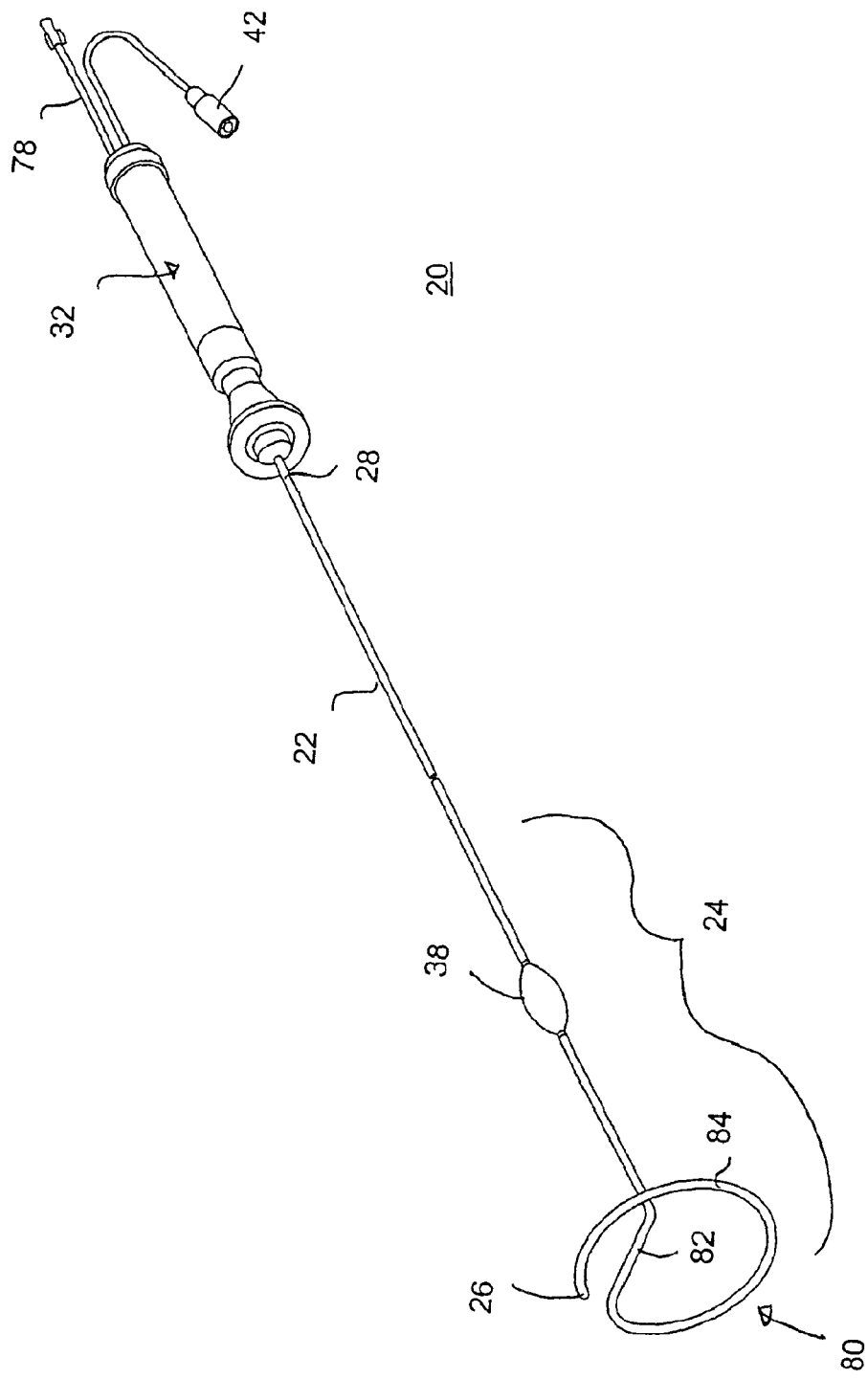
FIG. 2 is a perspective view of the catheter of the system of FIG. 1.
Figure 3:
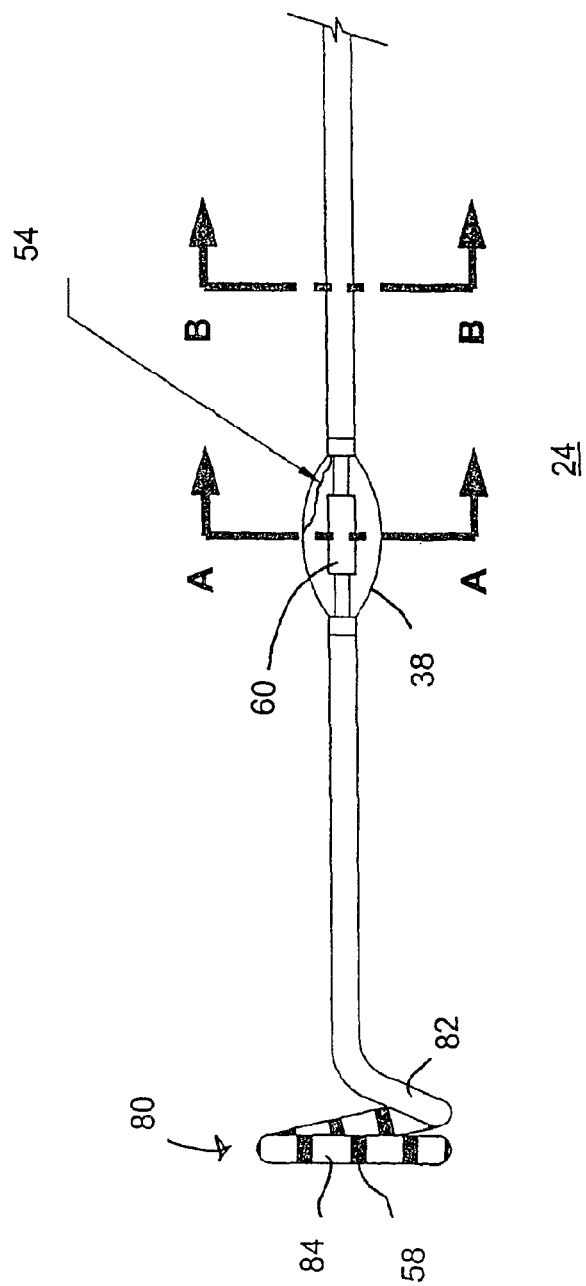
FIG. 3 is an enlarged view of the distal tip section of the catheter of FIGS. 1 and 2.
Figure 4:
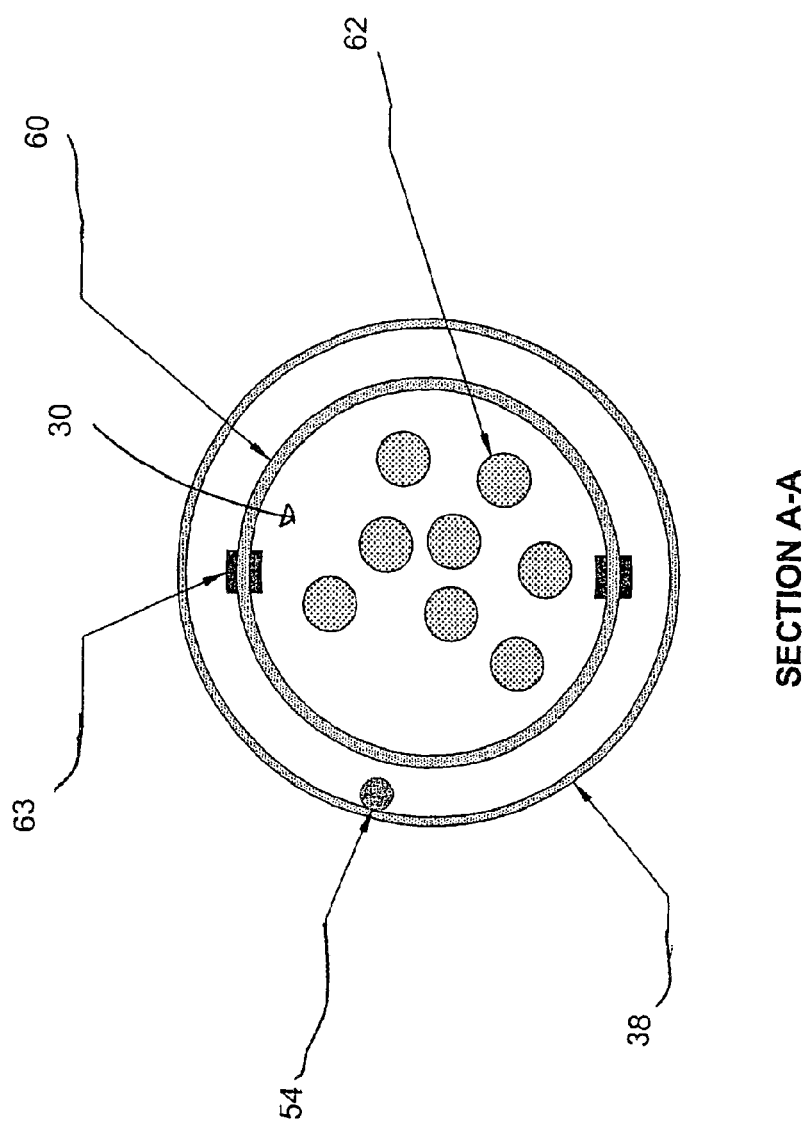
FIG. 4 is a cross-sectional view of the distal tip section of FIG. 3 taken along lines A-A thereof.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

The present invention provides a catheter system that has two separate elements for performing the mapping and ablation operations. A first element that includes ring electrodes is provided along a distal ring and functions to map the region of the heart that is to be treated. After the mapping has been completed, a second element that includes a transducer mounted inside a balloon is positioned at the location where ablation is to be performed, and is used to ablate the selected tissue. During the ablation, the distal ring functions to anchor the position of the balloon, while the balloon is inflated to a maximum diameter that is less than the diameter of the distal ring and the annulus where the treatment is taking place. As a result, blood can still flow unimpeded through the annulus.

Even though the present invention will be described hereinafter in connection with treating AF, it is understood that the principles of the present invention are not so limited, but can be used in other applications (e.g., treatment of accessory pathways, atrial flutter, ventricular tachycardia), and in other body pathways (e.g., right atrium, superior vena cava, right ventricle, left ventricle).

FIGS. 1-8 illustrate a catheter system 20 according to one embodiment of the present invention. The catheter system 20 has a tubular shaft 22 having a distal tip section 24, a distal end 26, a proximal end 28, and at least one lumen 30 extending through the shaft 22. A handle assembly 32 is attached to the proximal end 28 of the shaft 22 using techniques that are well-known in the catheter art.

The distal tip section 24 includes an expandable balloon 38 and a distal ring 80 that makes up the distal-most end of the shaft 22. A transducer 60 (e.g., piezoelectric or ultrasound) is housed inside the balloon 38. The balloon 38 can be made from any conventional material (such as but not limited to silicone, polyurethane, latex, polyamide and polyethylene), and heat bonded or otherwise attached to the shaft 22 using techniques that are well-known in the catheter art.

The distal ring 80 can be preformed into a generally curved or circular shape, resembling an open loop. The shape of the distal ring 80 corresponds to the circumferential geometry of a selected annulus (e.g., the PV) in the heart. In fact, the preformed shape of the distal ring 80 can be provided in a variety of curved geometries to overlie the anatomical geometry of the selected annulus. The distal ring 80 includes a transition section 82 that extends distally at an angle from the longitudinal axis of the shaft 22, and has a generally open-looped circular section 84 that extends from the transition section 82. As best seen from FIG. 3, the circular section 84 is oriented at an approximately perpendicular orientation from the longitudinal orientation of the shaft 22. The distal ring 80 can be made from the same material as the shaft 22. Such a material can be an electrically nonconductive, biocompatible, resilient plastic material which retains its shape and which does not soften significantly at human body temperature (e.g., Pebax™, polyethylene or polyester). As a non-limiting example, the geometry of the distal ring 80 can be created by thermoforming it into the desired shape.

A plurality of thermocouple wires 54 can have their distal tips secured to the interior surface of the balloon 38 (see FIG. 3), and are used to detect the temperature at the treatment site.

A plurality of ring electrodes 58 are provided in spaced-apart manner about the circular section 84 of the distal ring 80. The ring electrodes 58 can be made of a solid, electrically conducting material, like platinum or gold, that is attached about the circular section 84. Alternatively, the ring electrodes 58 can be formed by coating the exterior surface of the circular section 84 with an electrically conducting material, such as platinum or gold. The coating can be applied by sputtering, ion beam deposition or similar known techniques. The number of ring electrodes 58 can vary depending on the particular geometry of the region of use and the functionality desired.

As will be explained in greater detail below, the ring electrodes 58 function to map the region of the heart that is to be treated. After the mapping has been completed, the balloon 38 is positioned at the location where ablation is to be performed, and the distal ring 80 functions to anchor the position of the balloon 38. The balloon 38 is expanded, but even the greatest expanded diameter of the balloon 38 will be provided to be less than the diameter of the distal ring 80 when the distal ring 80 is fully deployed (see FIGS. 2, 3 and 7). The ablation is then carried out by energy that is emitted from the ultrasound transducer 60 through the inflation media (e.g., fluid, saline, contrast media or mixture) inside the balloon 38, and the balloon 38 itself.

A standard Luer fitting 34 is connected to the proximal end 36 of the handle assembly 32 using techniques that are well-known in the catheter art. The Luer fitting 34 provides a fluid line for inflation media to be introduced to inflate the balloon 38 at the distal tip section 24 of the shaft 22. The inflation media is delivered via an inflation lumen 76 that extends from the handle assembly 32 (and coupled to the line 78 of the Luer fitting 34), and terminates at the balloon 38.

A connector assembly 40 is also connected to the proximal end 36 of the handle assembly 32 using techniques that are well-known in the catheter art. The connector assembly 40 has a proximal connector 42 that couples the handle assembly 32 to the connector 44 of a control line 46 that leads to an ultrasound generator 52. An EKG monitor 50 is coupled to the ultrasound generator 52 via another line 48. The EKG monitor 50 can be a conventional EKG monitor which receives (via the ultrasound generator 52) electrical signals detected by the ring electrodes 58 at the distal tip section 24, and processes and displays these electrical signals to assist the physician in locating the site of potentials in a PV. The ultrasound generator 52 can be a conventional ultrasound generator that creates and transmits ablating energy to the ultrasound transducer 60 that is positioned inside the balloon 38. The ultrasound transducer 60 will emit the energy to ablate the tissue that extends radially from the position of the balloon 38.

Electrical wires (not shown) extend from the ultrasound generator 52 along the lines 46 and 48, and conductor wires 62 and ultrasound wires 63 extend through the connector assembly 40, the handle assembly 32 and the lumen 30 of the shaft 22 to the distal tip section 24 of the shaft 22 to couple the ring electrodes 58 and the transducer 60, respectively. In addition, the thermocouple wires 54 can extend from the balloon 38 through the lumen 30 of the shaft 22 and the handle assembly 32 to the proximal connector 42, where they can be electrically coupled by the wires in the line 46 to the ultrasound generator 52 where the temperature can be displayed.

Figure 5:
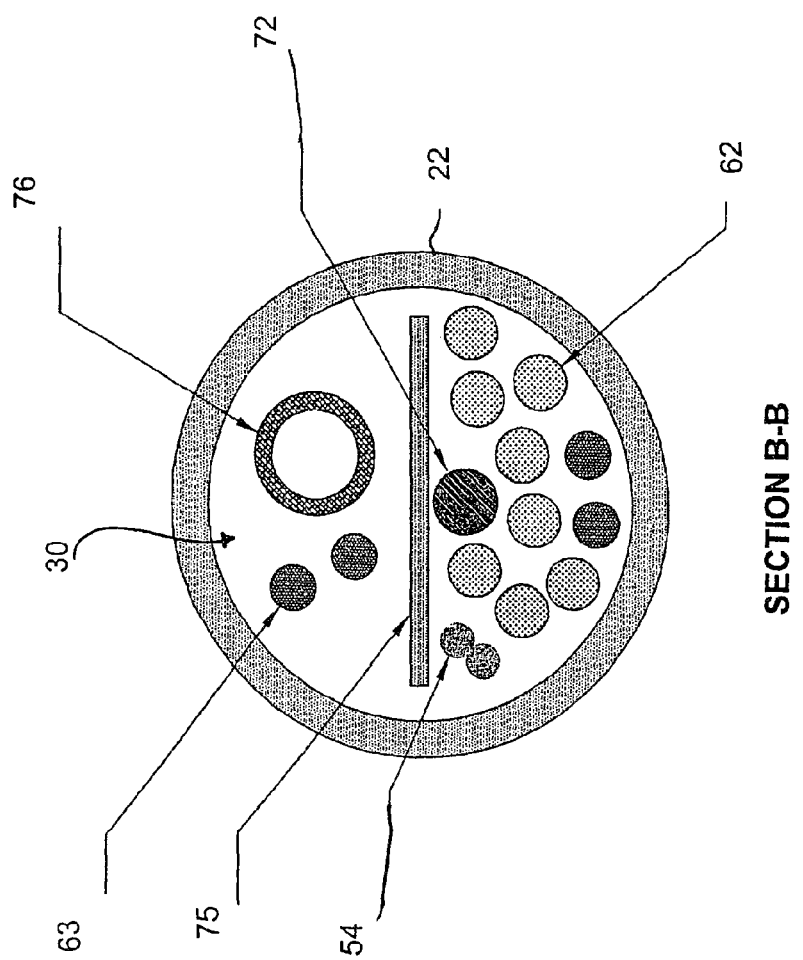
FIG. 5 is a cross-sectional view of the distal tip section of FIG. 3 taken along lines B-B thereof.
Figure 8:
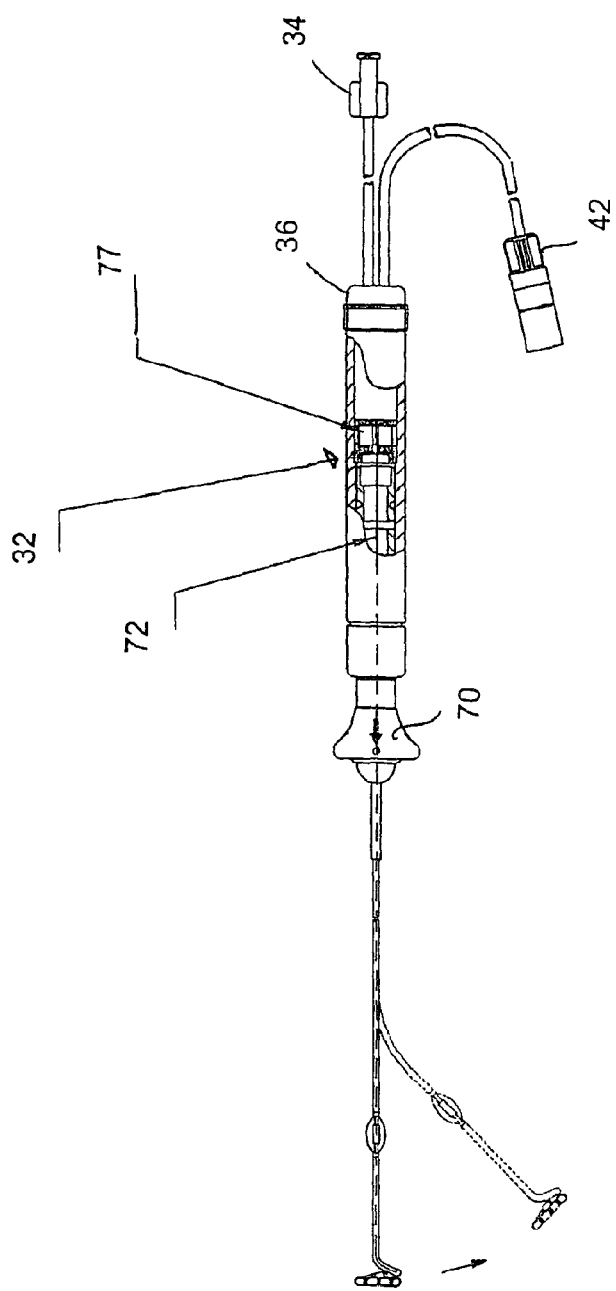
FIG. 8 illustrates the steering mechanism of the catheter of FIGS. 1 and 2.

The handle assembly 32 also includes a steering mechanism 70 that functions to deflect the distal tip section 24 of the shaft 22 for maneuvering and positioning the distal tip section 24 at the desired location in the heart. Referring to FIGS. 1, 5 and 8, the steering mechanism 70 includes a steering wire 72 that extends in the main lumen 30 of the shaft 22 from its proximal end at the handle assembly 32 to its distal end which terminates in the distal tip section 24 before the location of the balloon 38. The proximal end of the steering wire 72 is wound around or secured to an anchor 77 that is fixedly positioned inside the handle assembly 32. The steering mechanism 70 also includes a flat wire 75 that extends in the lumen 30 from the anchor 77 to its distal end at a location slightly proximal to the balloon 38 (as shown in FIG. 5). The flat wire 75 is attached to the steering wire 72 at the distal ends of the flat wire 75 and the steering wire 72 so as to be controlled by the steering wire 72. Specifically, by pushing the steering mechanism 70 forward in a distal direction, the steering mechanism 70 will pull the steering wire 72 in a proximal direction, causing the distal tip section 24 to deflect to one direction (see in phantom in FIG. 8). By pulling back the steering mechanism 70 in a proximal direction, the steering wire 72 is deactivated and the distal tip section 24 returns to its neutral position or deflects to the opposite direction.

The distal ring 80 can be preformed to a fixed size (i.e., diameter) and shape that cannot be changed. Alternatively, the diameter of the distal ring 80 can be adjusted using techniques and incorporating mechanisms that are well-known in the catheter art.

Figure 6:
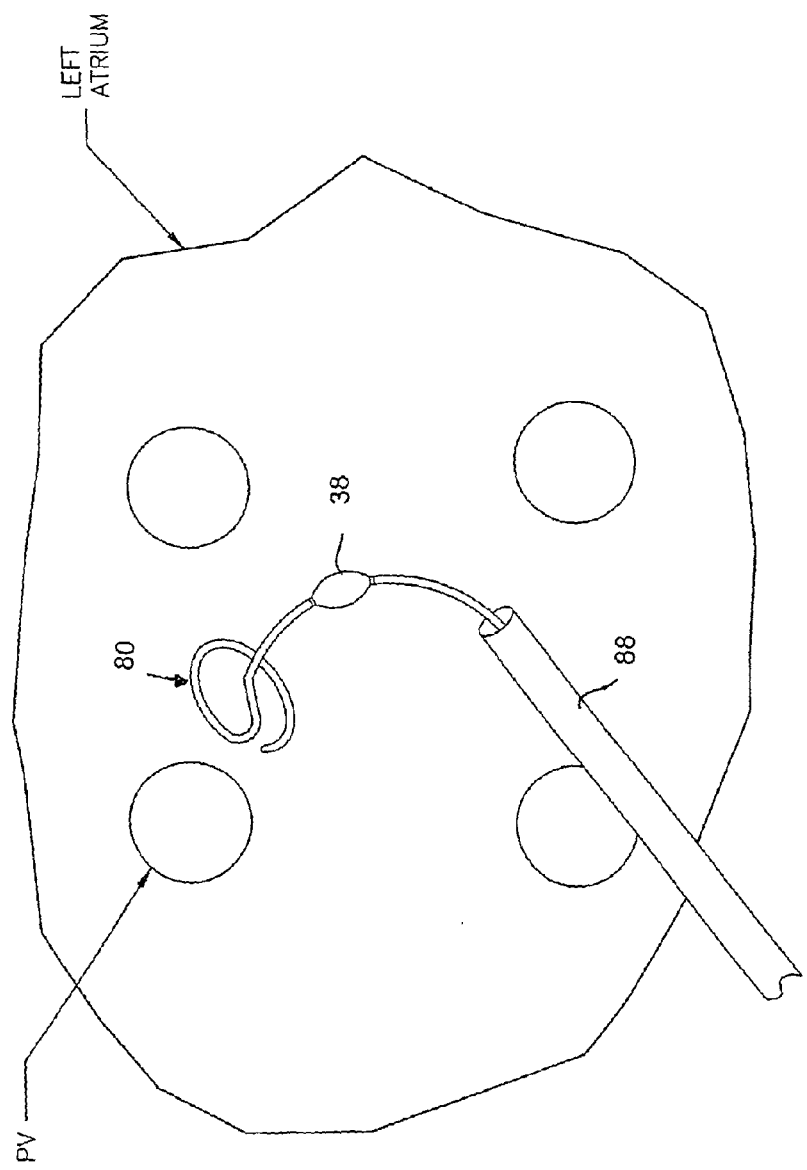
FIG. 6 illustrates how the catheter of FIGS. 1 and 2 is deployed for use inside the heart of a patient.
Figure 7:
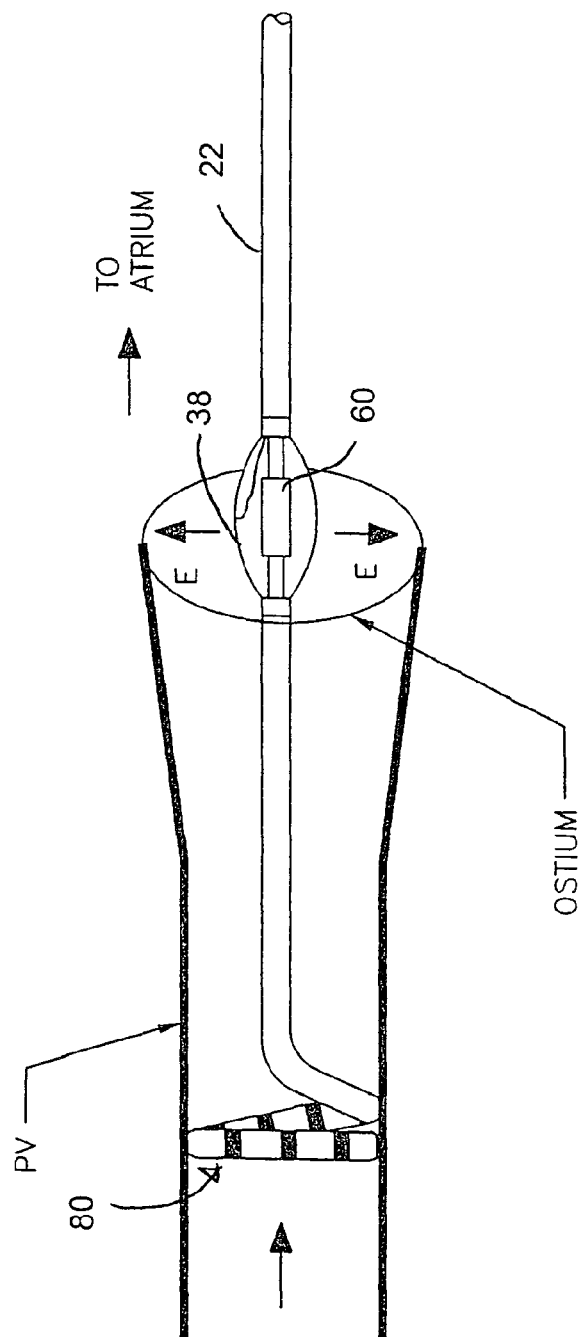
FIG. 7 is a cross-sectional view illustrating the catheter of FIGS. 1 and 2 in use in a pulmonary vein during the mapping and ablation steps.

FIGS. 6 and 7 illustrate how the catheter system 20 is used. First, a guide sheath 88 is provided to deliver the shaft 22 and distal ring 80 to the desired location (e.g., the left atrium) in the heart. The shaft 22 is slid into the hollow lumen of the guide sheath 88, and the guide sheath 88 can slide forward and backward along the longitudinal axis of the shaft 22. When the guide sheath 88 is slid forwardly towards the distal ring 80, the distal ring 40 is progressively straightened out and drawn into the lumen of the guide sheath 88. Thus, when confined with the guide sheath 88, the distal ring 80 assumes the generally linear low profile shape of the guide sheath 88, which allows a physician to employ conventional percutaneous access techniques to introduce the catheter 20 into a selected region of the heart through a vein or artery. When the guide sheath 88 is slid rearwardly away from the distal ring 80, the distal ring 80 is uncovered and its resilient memory will cause the distal ring 80 to re-assume its preformed generally circular shape.

To introduce and deploy the distal tip section 24 within the heart, the physician uses a conventional introducer to establish access to a selected artery or vein. With the guide sheath 88 confining the distal ring 80, and with the balloon 38 deflated, the physician introduces the shaft 22 and the guide sheath 88 through a conventional hemostatic valve on the introducer and progressively advances the guide sheath 88 through the access vein or artery into the desired atrium, such as the left atrium as shown in FIG. 6. The physician observes the progress of the guide sheath 88 using fluoroscopic or ultrasound imaging. The guide sheath 88 can include a radio-opaque compound, such as barium, for this purpose. Alternatively, radio-opaque markers can be placed at the distal end of the guide sheath 88.

The shaft 22 and the guide sheath 88 can be maneuvered to the left atrium by the steering mechanism 70. Once located in the left atrium, the physician slides the guide sheath 88 back to free the distal ring 80 which resiliently returns to its preformed shape. The distal ring 80 is then maneuvered into contact with the selected annulus (e.g., the ostium) with the aid of fluoroscopy. Good contact is established when the ring electrodes 58 contact the selected annulus, and at this time, the physician operates a control located on the ultrasound generator 52 to effectuate the mapping of the selected annulus by the ring electrodes 58. The results of the mapping operation are processed and displayed at the EKG monitor 50. A differential input amplifier (not shown) in the EKG monitor 50 processes the electrical signals received from the ring electrodes 58 via the wires 62, and converts them to graphic images that can be displayed. The thermocouple wires 54 can also function to monitor the temperature of the surrounding tissue, and provide temperature information to the ultrasound generator 52. Throughout this mapping operation, the balloon 38 remains deflated.

Once the mapping operation has been completed and the desired position of the balloon 38 has been confirmed, the physician can then inflate the balloon 38 using inflation media. The balloon 38 is preferably manufactured using known techniques to a predetermined diameter so that its diameter at its maximum expansion will be less than the diameter of the distal ring 80 and the annulus or vessel (e.g., the PV in FIG. 7) where the ablation is to take place. The physician then controls the ultrasound generator 52 to generate ultrasound energy that is propagated through the wires 63 to the ultrasound transducer 60 that is positioned inside the balloon 38. The energy radiates in a radial manner from the transducer 60, propagates through the inflation media (which acts as an energy transmitting medium) inside the balloon 38, exits the balloon 38 and then reaches the selected tissue (typically in a waveform) to ablate the tissue. See the arrows E in FIG. 7 which illustrate the radiation of the energy from the transducer 60.

During the ablation, the distal ring 80 functions to anchor the distal tip section 24 inside the PV at the desired location so that the ablation can be performed accurately. In contrast to known catheter systems where the same element is used to anchor and ablate, by providing a separate element (i.e., the distal ring 80) to anchor the distal tip section 24, the function of the ablation element (i.e., the balloon 38 and transducer 60) will not be affected by the anchoring device, thereby ensuring that the ablation is performed accurately and effectively. In addition, since the maximum diameter of the balloon 38 is always smaller than the smallest diameter of the distal ring 80, blood will be able flow through the distal ring 80 and around the surfaces of the balloon 38.

When the ablation has been completed, the balloon 38 is deflated and the distal tip section 24 withdrawn from the heart.

FIGS. 9-14 illustrate modifications made to the catheter system 20 of FIGS. 1-5 to allow contrast medium to be introduced while the catheter is located within the vessel ostium and while the balloon 38 is inflated. The catheter system 20a in FIGS. 9-14 essentially provides an additional tubing and lumen to facilitate the injection of the contrast medium. The catheter system 20 in FIGS. 1-5 did not provide an additional lumen, so the contrast medium for vessel geometry and catheter location could not be readily verified. Hence, the catheter system 20a makes it easier to verify vessel geometry and catheter location since the blood flow from within the vessel will not wash out when the contrast medium is injected due to balloon inflation.

Since the catheter system 20a merely includes modifications to the catheter system 20, the descriptions relating to the same elements and their functions will not be repeated herein. Instead, the same numerals used to designate elements in FIGS. 1-5 will be used to designate the same elements in FIGS. 9-14, except that an "a" will be added to the designations in FIGS. 9-14.

Figure 9:
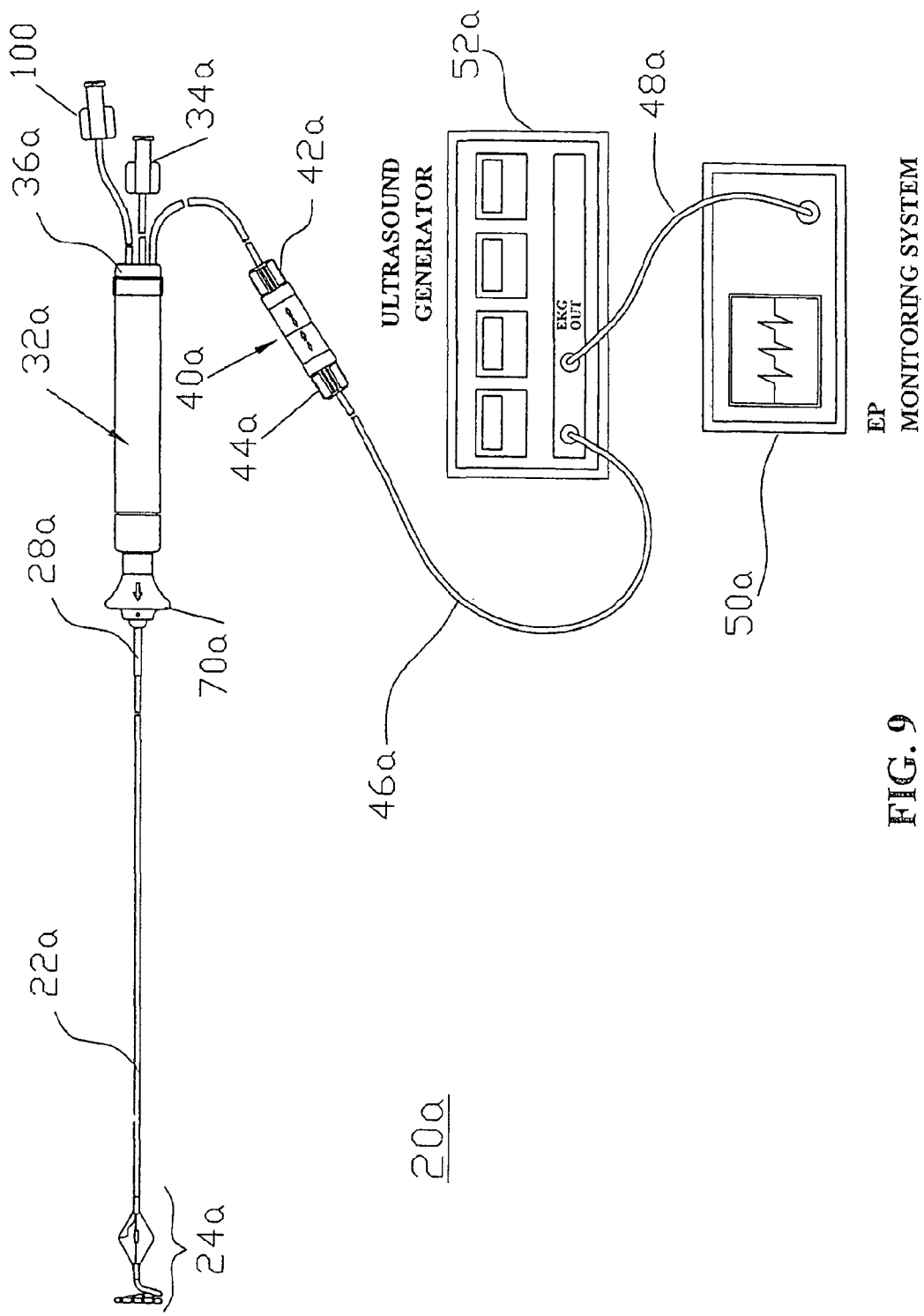
FIG. 9 illustrates a mapping and ablation system according to another embodiment of the present invention.
Figure 10:
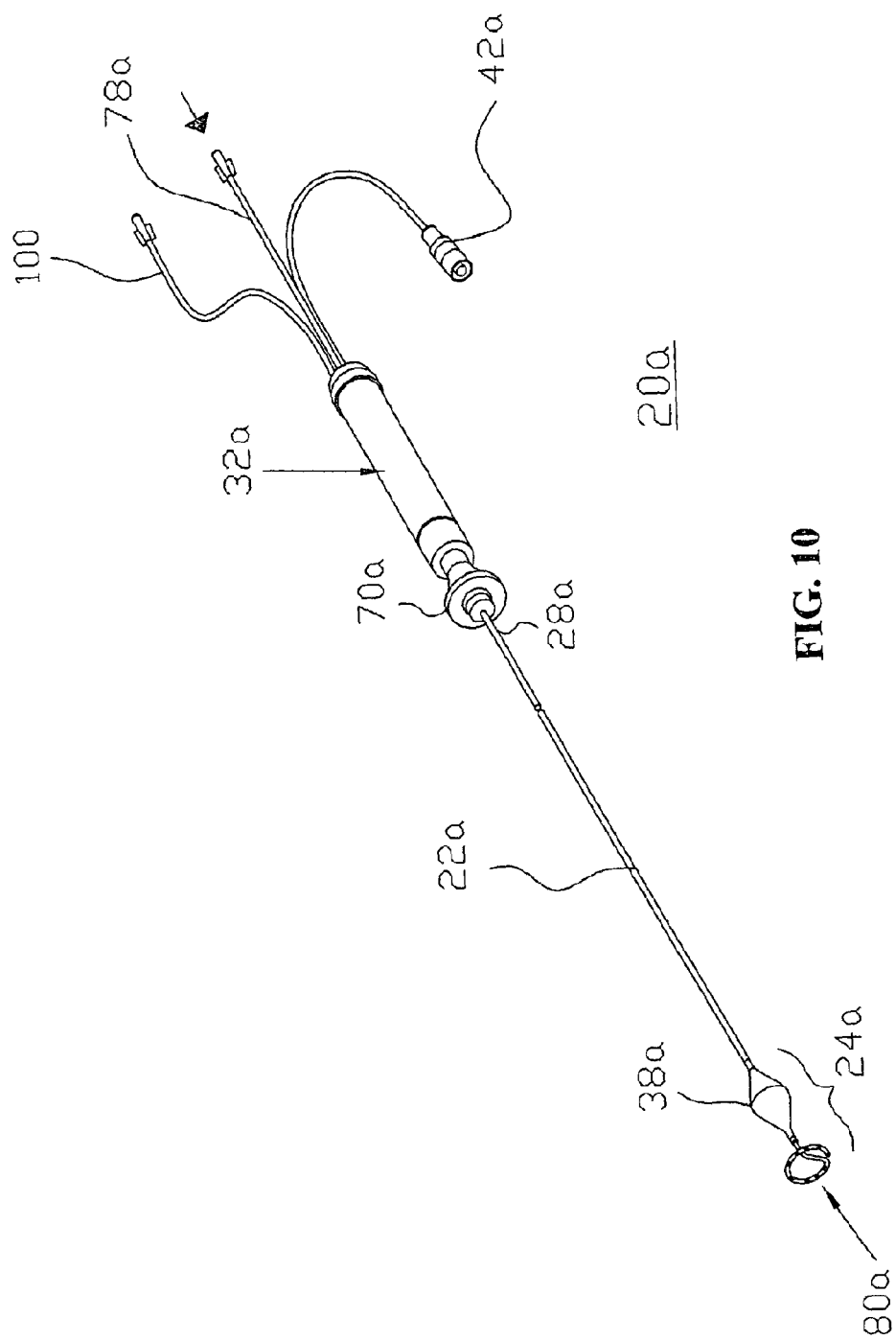
FIG. 10 is a perspective view of the catheter of the system of FIG. 9.
Figure 11:
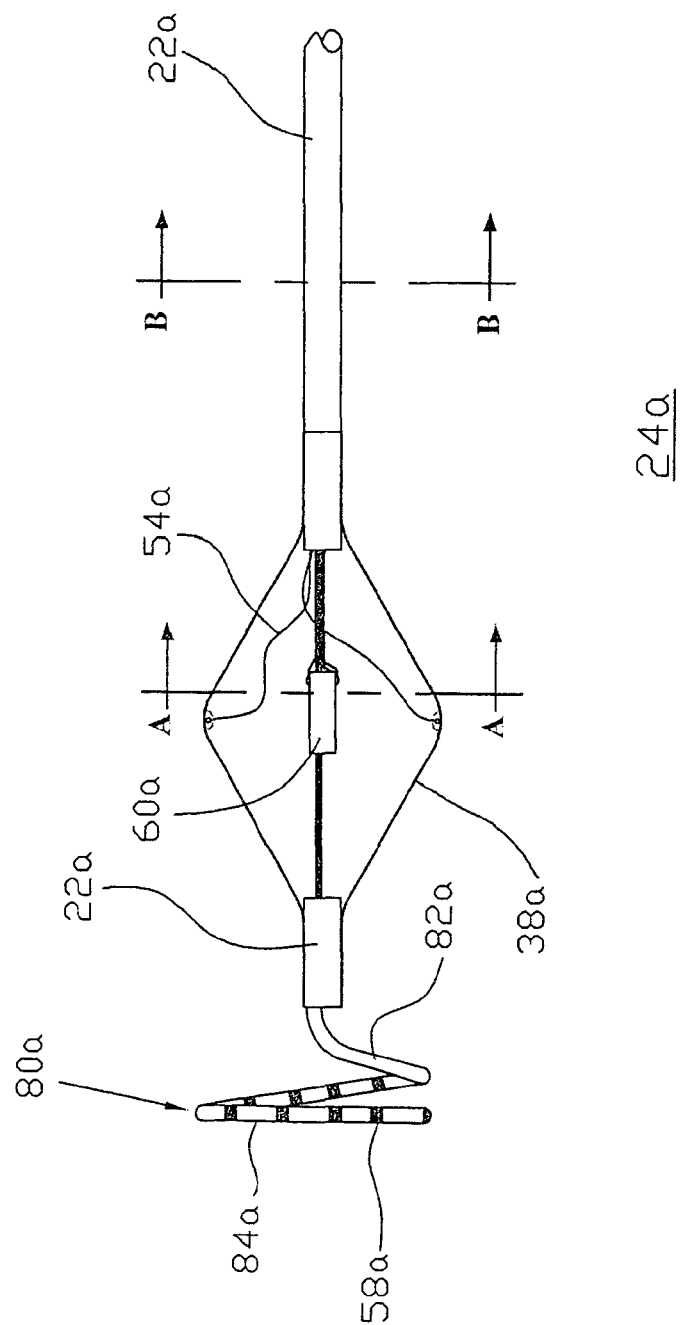
FIG. 11 is an enlarged view of the distal tip section of the catheter of FIGS. 9 and 10.
Figure 12:
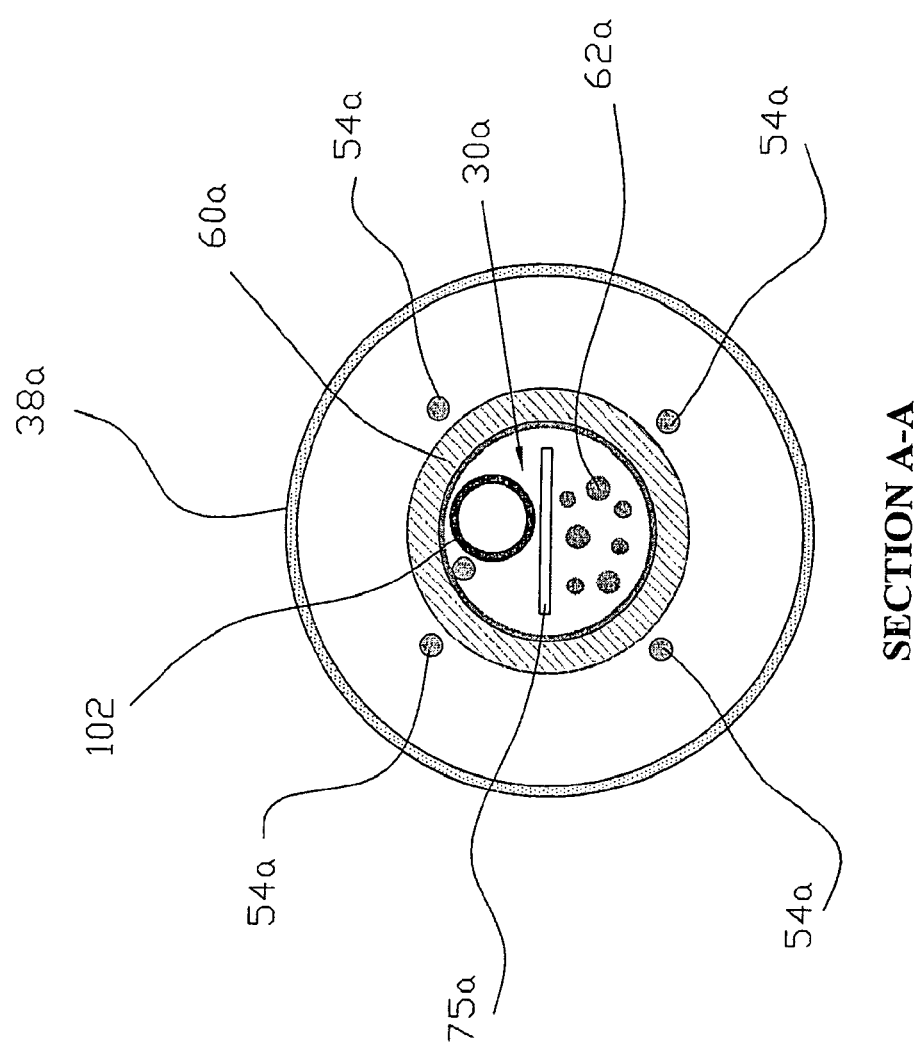
FIG. 12 is a cross-sectional view of the distal tip section of FIG. 11 taken along lines A-A thereof.
Figure 13:
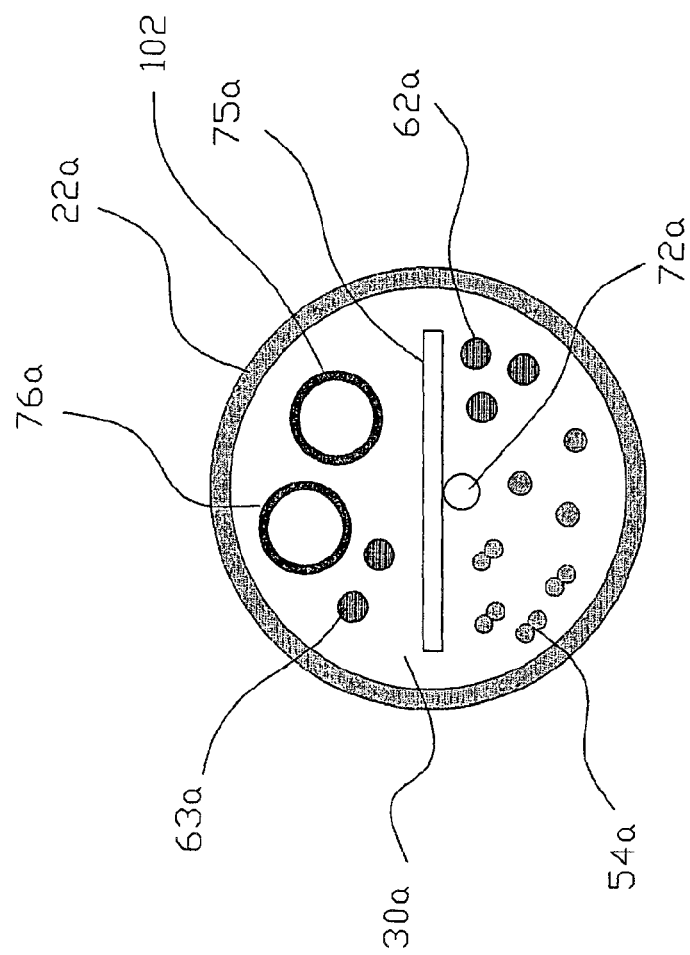
FIG. 13 is a cross-sectional view of the distal tip section of FIG. 11 taken along lines B-B thereof.
Figure 14:
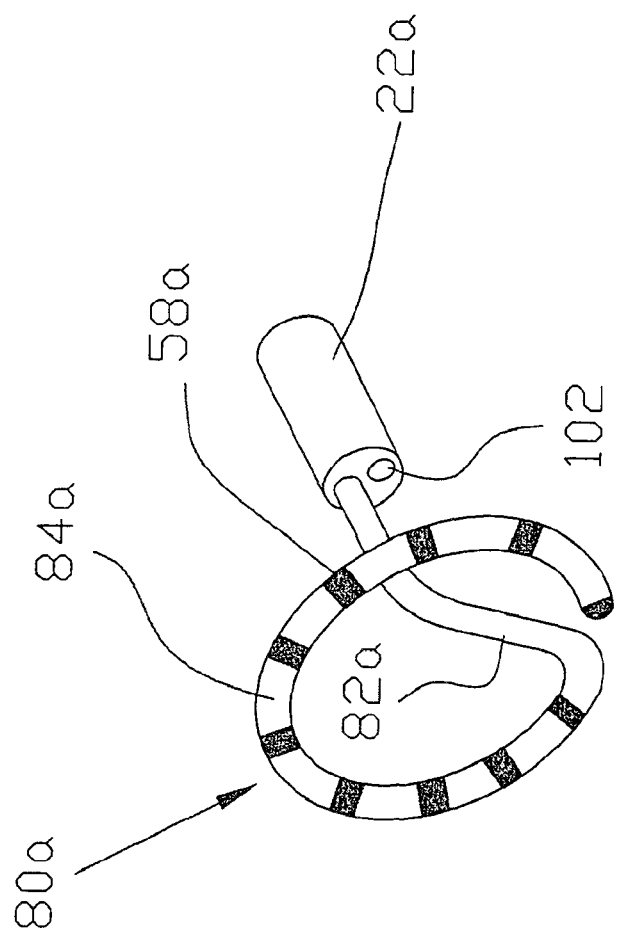
FIG. 14 is an enlarged perspective view of the distal tip section of the catheter of FIGS. 9 and 10.

The catheter system 20a provides an additional tubing 100 that extends from the handle assembly 32a (see FIGS. 9-10). This tubing 100 is connected to a lumen 102 that extends through the shaft 22a, the transducer 60a inside the balloon 38a, and exits at the distal-most end of the shaft 22a. See FIGS. 11 and 14. The contrast medium can be injected via the tubing 100 and the lumen 102 by a syringe (not shown), and exits the catheter into the blood vessel at the location of the distal ring 80a to provide visibility of the location of the distal ring 80a and the balloon 38a. A guidewire (not shown) can be inserted into this lumen 102 to increase the mobility of the shaft 22a into branches of the main vessel.

In addition, the flat wire 75a extends in the lumen 30a from the distal section of the shaft 22a (not shown in FIGS. 9-14).

Figure 15:
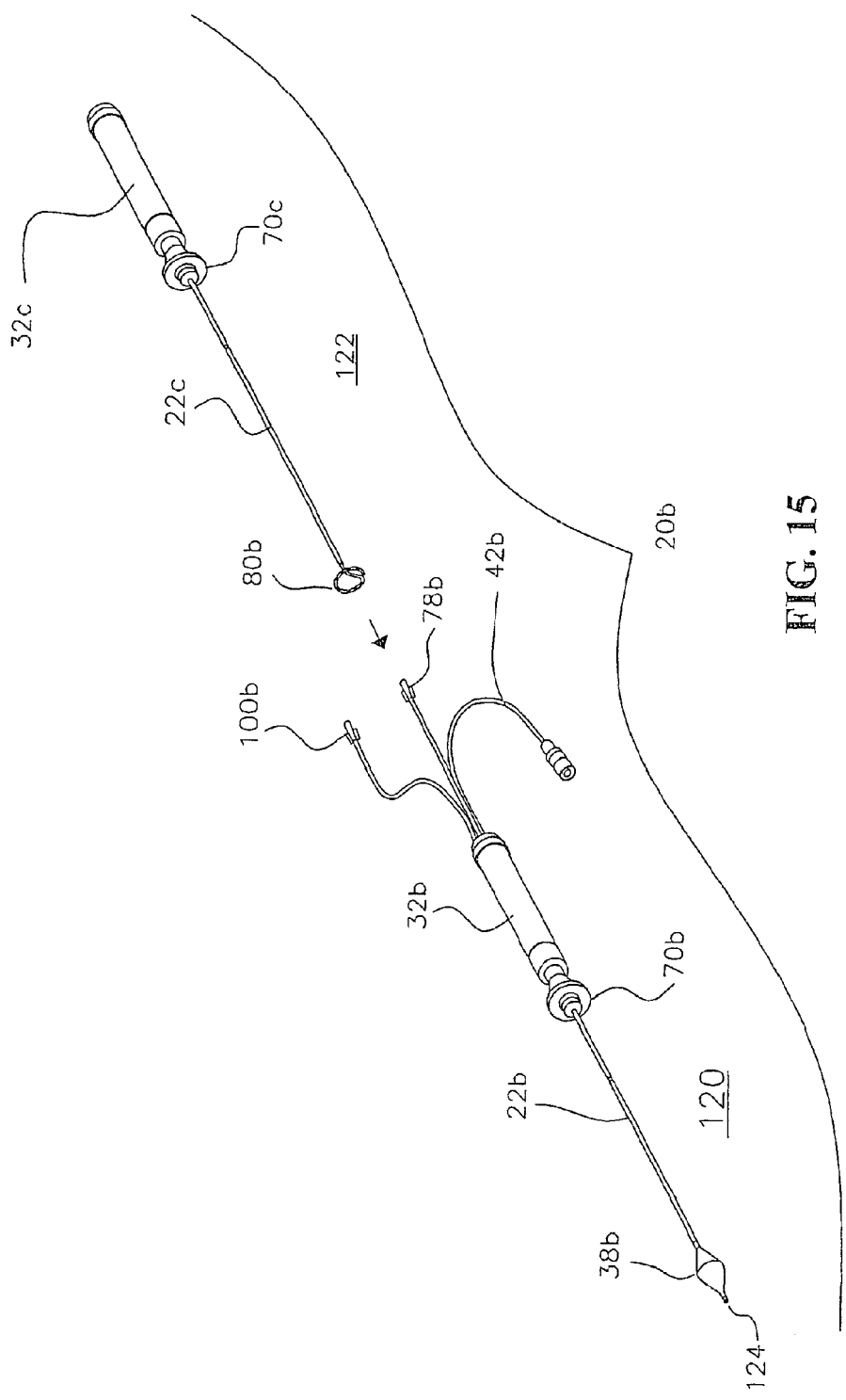
FIG. 15 illustrates a mapping and ablation system according to another embodiment of the present invention.
Figure 16:
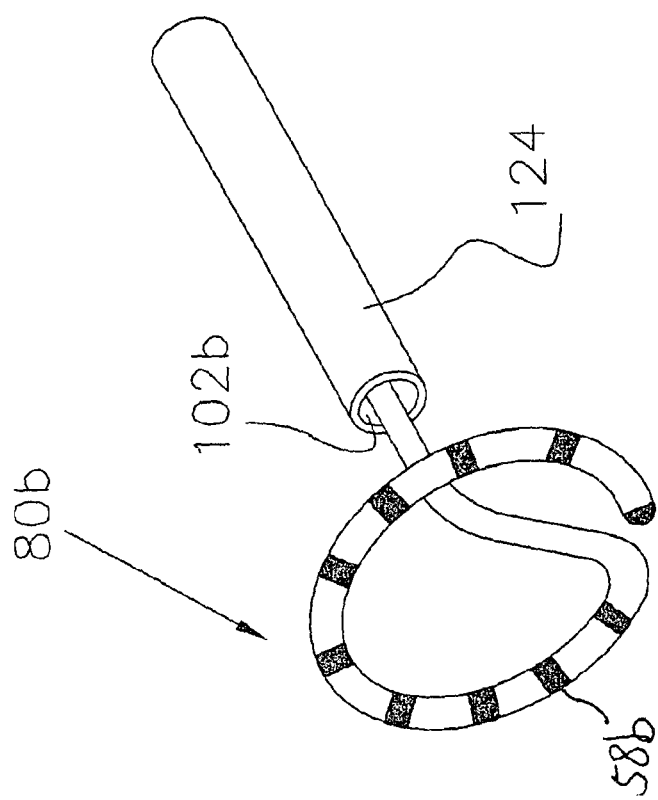
FIG. 16 is an enlarged perspective view of the distal tip section of the catheter of FIG. 15.
Figure 17:
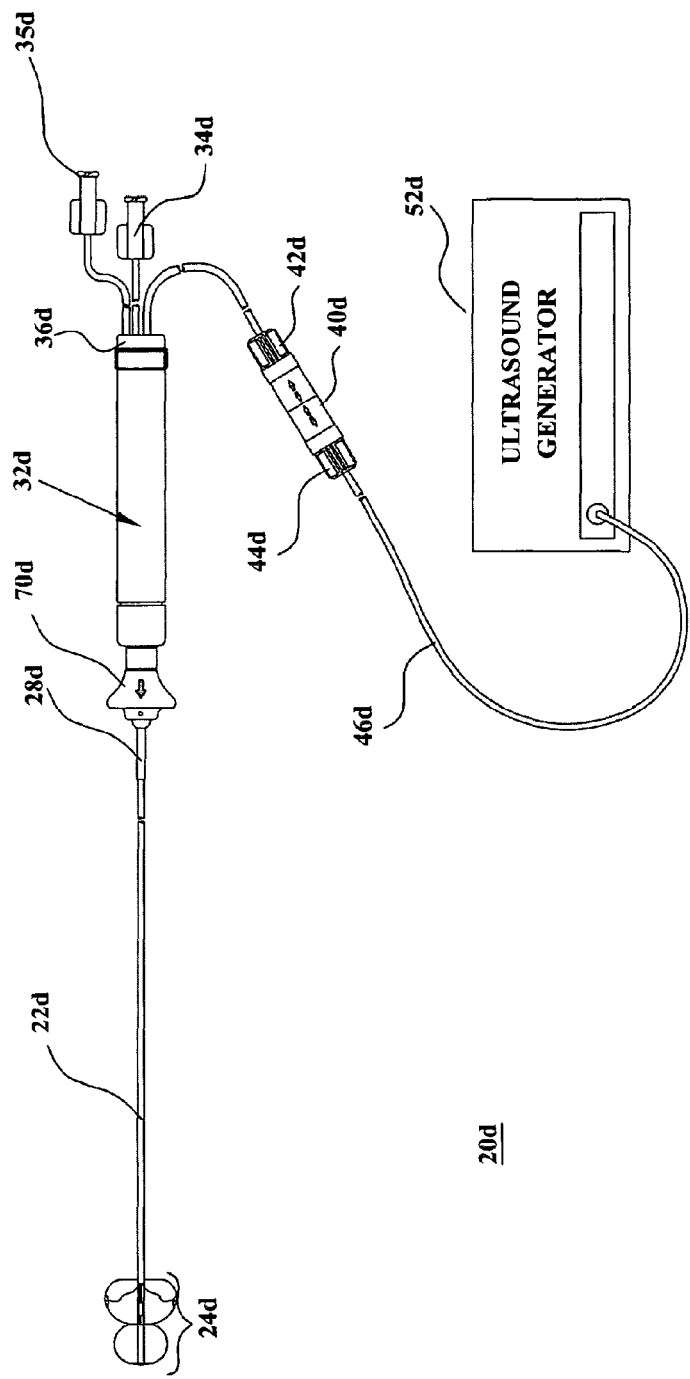
FIG. 17 illustrates an ablation system according to yet another embodiment of the present invention.
Figure 18:
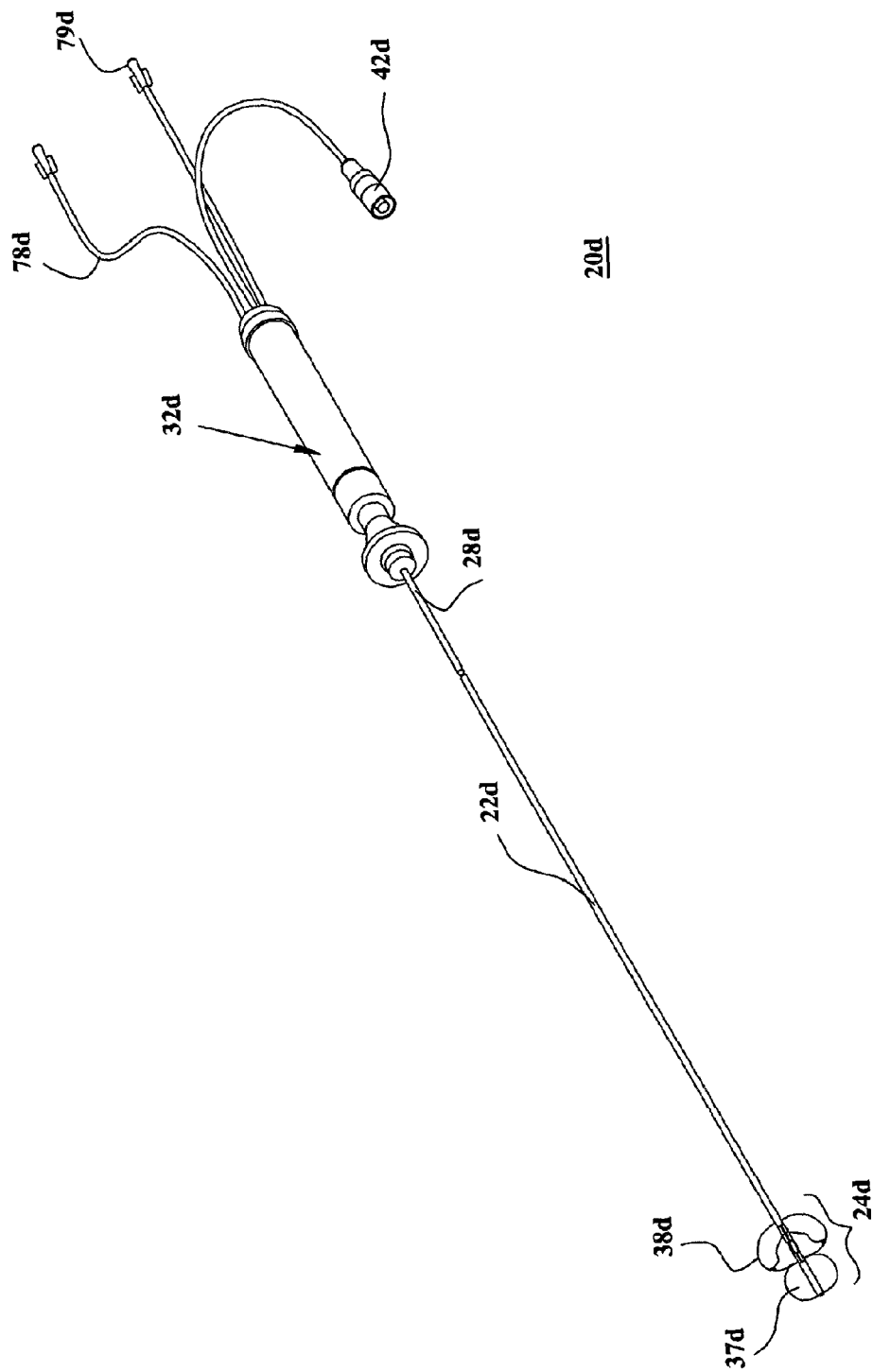
FIG. 18 is a perspective view of the catheter of the system of FIG. 17.
Figure 19:
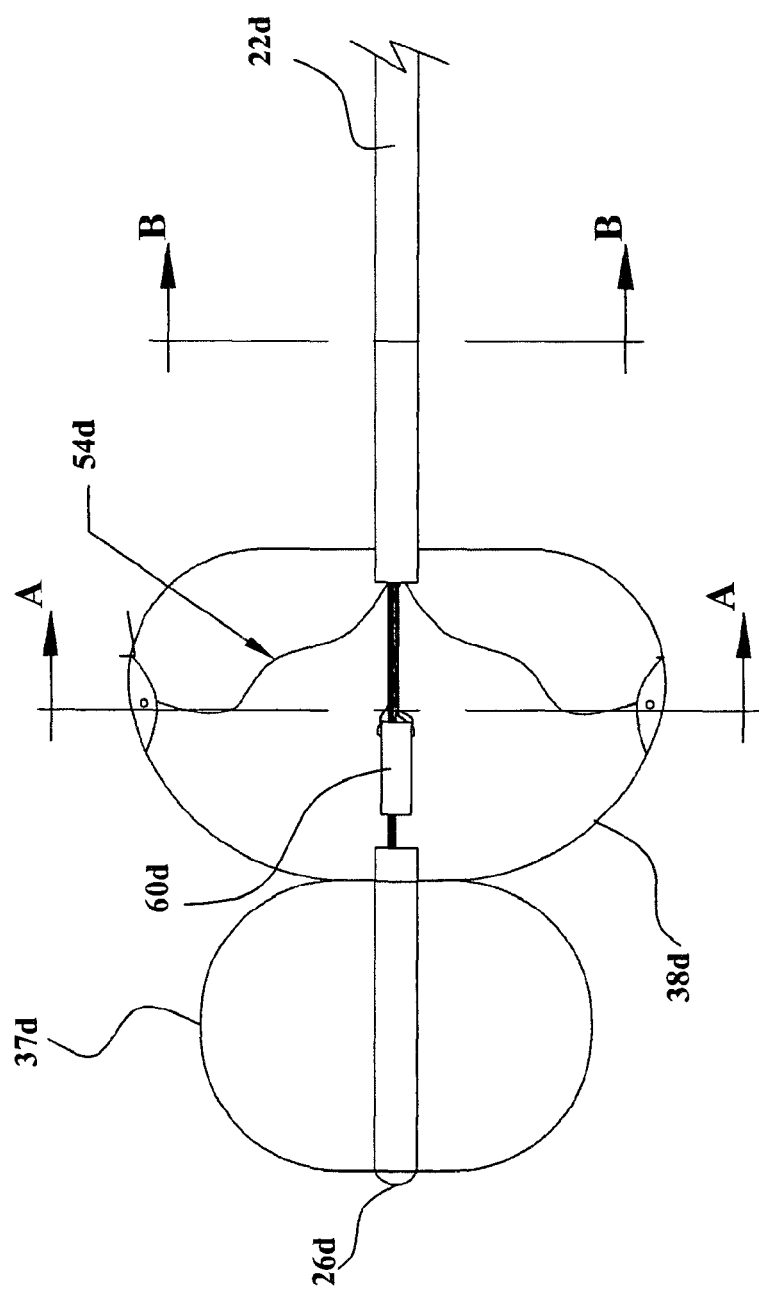
FIG. 19 is an enlarged view of the distal tip section of the catheter of FIGS. 17 and 18.
Figure 20:
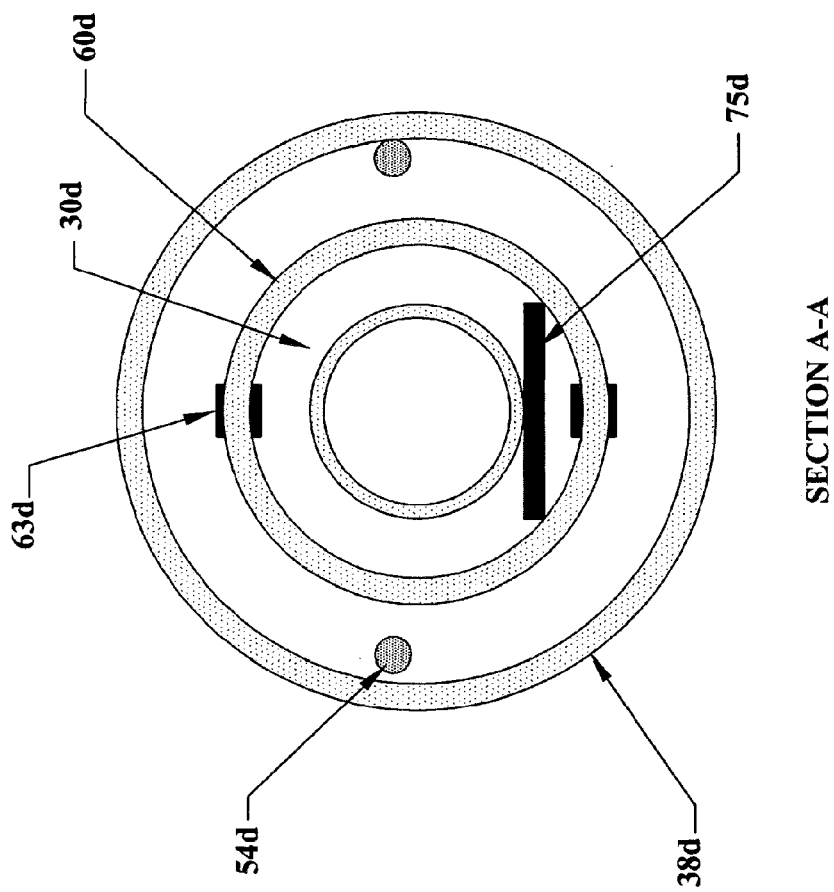
FIG. 20 is a cross-sectional view of the distal tip section of FIG. 19 taken along lines A-A thereof.
Figure 21:
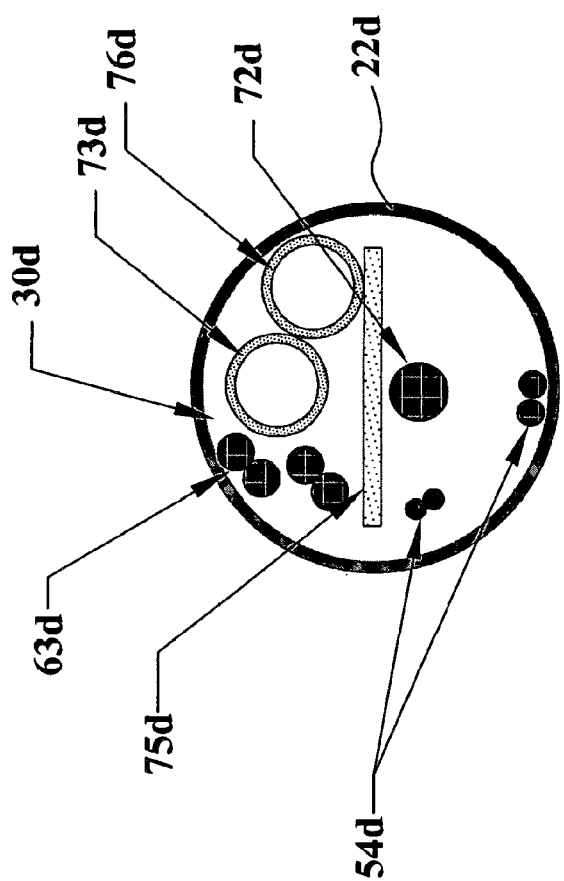
FIG. 21 is a cross-sectional view of the distal tip section of FIG. 19 taken along lines B-B thereof.

FIGS. 15-16 illustrate yet another modification that can be made to the system 20 in FIGS. 1-5. The catheter system 20b in FIGS. 15-16 is comprised of two separate catheters, a first catheter 120 that carries the balloon 38b and the transducer 60b, and a second catheter 122 that carries the distal ring 80b.

Since the catheter system 20b merely includes modifications to the catheter system 20a, the descriptions relating to the same elements and their functions will not be repeated herein. Instead, the same numerals used to designate elements in FIGS. 9-14 will be used to designate the same elements in FIGS. 15-16, except that a "b" or a "c" will be added to the designations in FIGS. 15-16. The only notable differences are (i) the catheter 120 has the same structure as the catheter 20a with the exception of the distal ring 80a, and (ii) the catheter 122 has the same structure as the catheter 120 except for the balloon 38a, the transducer 60a, and the thermocouples.

The distal ring 80b and the shaft 22c of the catheter 122 can be inserted through the lumen 102b of the catheter 120. In this regard, the distal ring 80b can progressively straightened out and drawn into the lumen 102b of the catheter 120. Thus, when confined within the catheter 120, the distal ring 80b assumes the generally linear low profile shape of the catheter 120. When the distal ring 80b exits the distal-most end 124 of the catheter 120 (see FIG. 16), the distal ring 80b is uncovered and its shape memory (e.g., Nitinol) will cause the distal ring 80b to re-assume its preformed generally circular shape.

The catheter 122 can also be steered so that the diameter of the distal ring 80b can be varied. This can be accomplished by providing a pulling wire (not shown, but can be the same as 72 or 72a), and then pulling the pulling wire. The catheter 120 can also be steered so that the distal end 124 can be deflected. The steering of the catheters 120, 122 can be accomplished using steering mechanisms 70b, 70c that can be the same as the steering mechanism 70 described in FIGS. 1-5.

The main lumen 30b of the catheter 120 can be used to accommodate a guidewire (not shown), and can also be used for delivering contrast medium. Therefore, the catheter system 20b does not require an additional tubing (such as 100) or lumen (such as 102) as in the catheter system 20a, although it is also possible to provide an additional tubing (such as 100) or lumen (such as 102) if such is desired.

The following illustrates one example of a possible use of the catheter system 20b. A transseptal sheath (with a dilator in the sheath lumen) is typically inserted into the patient's femoral vein and placed into the right atrium. Using a transseptal (Brockenbrough) needle, a puncture is produced in the fossa ovalis in the septal wall to provide access from the right atrium to the left atrium. The sheath is then brought inside the left atrium, the needle removed, and a guidewire is inserted through the lumen of the dilator to the target pulmonary vein or its branches. The distal opening of the dilator inside the sheath follows the guidewire to the pulmonary vein. When the catheter 20a is used, the dilator and the guidewire are removed and the catheter is inserted into the transseptal sheath into the pulmonary vein. When the catheter 120 is used, only the dilator is removed and the lumen 102b of the distal end of the catheter follows the path of the guidewire and into the target PV. Once the catheter 20a or 120 is situated in the pulmonary vein ostium, the balloon 38a or 38b is inflated until it engages the ostial wall. Contrast media is injected in the lumen 102 or 102b to visually verify the location of the transducer 60a with respect to the pulmonary vein anatomy.

For the catheter 20a, the location of the transducer 60a can be verified via contrast medium injection while the distal ring 80a records the PV potentials. This has not been possible with the conventional systems.

For the catheter system 20b, the catheter 122 is inserted through the tubing 100b and the distal ring 80b exits from the lumen 102b. The diameter of the distal ring 80b can be adjusted to fit the different sizes of the pulmonary vein. The electrodes 58b are again used to pick up the PV potentials. Once the potentials (or intracardiac signals) are recorded, the catheter 122 can be removed, and if needed, contrast medium can be injected for locating the transducer. Energy can then be delivered to perform the ablation, as described above.

FIGS. 17-24 illustrate a catheter system 20d according to yet another embodiment of the present invention. The catheter system 20d is similar to the catheter system 20 in FIGS. 1-8, except that the catheter system 20d has a second balloon 37d instead of a distal ring. As a result, the descriptions relating to the same elements and their functions in FIGS. 1-8 and FIGS. 17-24 will not be repeated herein. Instead, the same numerals used to designate elements in FIGS. 1-8 will be used to designate the same elements in FIGS. 17-24, except that a "d" will be added to the designations in FIGS. 17-24.

The distal tip section 24d includes a first expandable balloon 38d that can be the same as the balloon 38, and a second expandable balloon 37d. The balloons 37d and 38d can be positioned side-by-side next to each other. A transducer 60d (e.g., piezoelectric or ultrasound) is also housed inside the first balloon 38d. Both balloons 37d and 38d can be made from any conventional material (such as but not limited to silicone, polyurethane, latex, polyamide and polyethylene), and heat bonded or otherwise attached to the shaft 22d using techniques that are well-known in the catheter art. A plurality of thermocouple wires 54d can have their distal ends secured to the interior surface of the first balloon 38d (see FIG. 19), and are used to detect the temperature at the treatment site.

Standard Luer fittings 34d and 35d are connected to the proximal end 36d of the handle assembly 32d using techniques that are well-known in the catheter art. The Luer fittings 34d and 35d provide fluid lines for inflation media to be introduced to inflate the balloons 37d and 38d at the distal tip section 24d of the shaft 22d. For example, the inflation media is delivered via an inflation lumen 76d (see FIG. 21) that extends from the handle assembly 32d (and coupled to the line 78d of the Luer fitting 34d), and terminates at the balloon 38d. Similarly, the inflation media is delivered via an inflation lumen 73d that extends from the handle assembly 32d (and coupled to the line 79d of the Luer fitting 35d), and terminates at the balloon 37d.

The connector assembly 40d and its connection to the ultrasound generator 52d can be the same as described in FIGS. 1-8 above. In addition, the steering mechanism 70d can also be the same as described in FIGS. 1-8 above, except that the steering wire 72d extends in the main lumen 30d of the shaft 22d from its proximal end at the handle assembly 32d to its distal end which terminates in the distal tip section 24d before the location of the balloon 38d.

Figure 22:
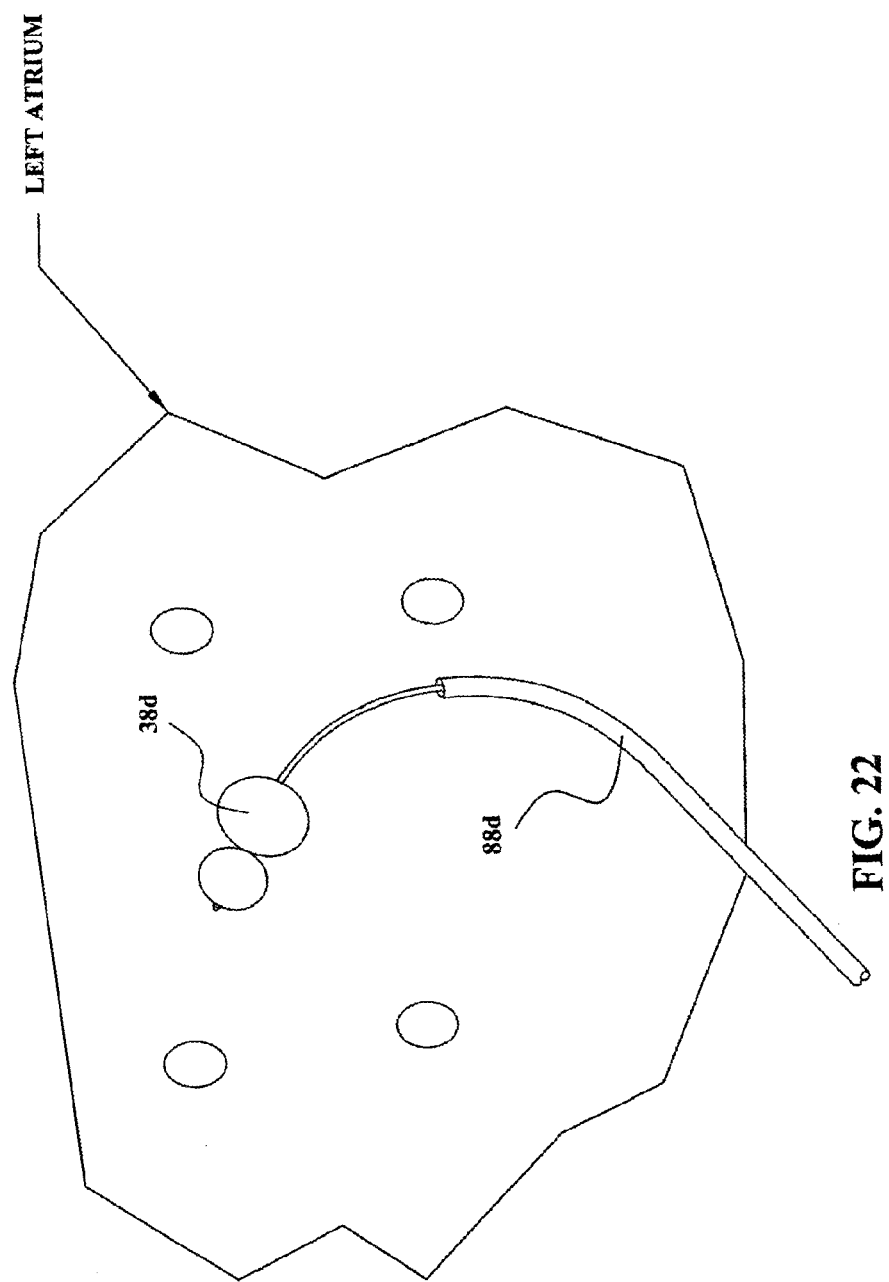
FIG. 22 illustrates how the catheter of FIGS. 17 and 18 is deployed for use inside the heart of a patient.
Figure 23:
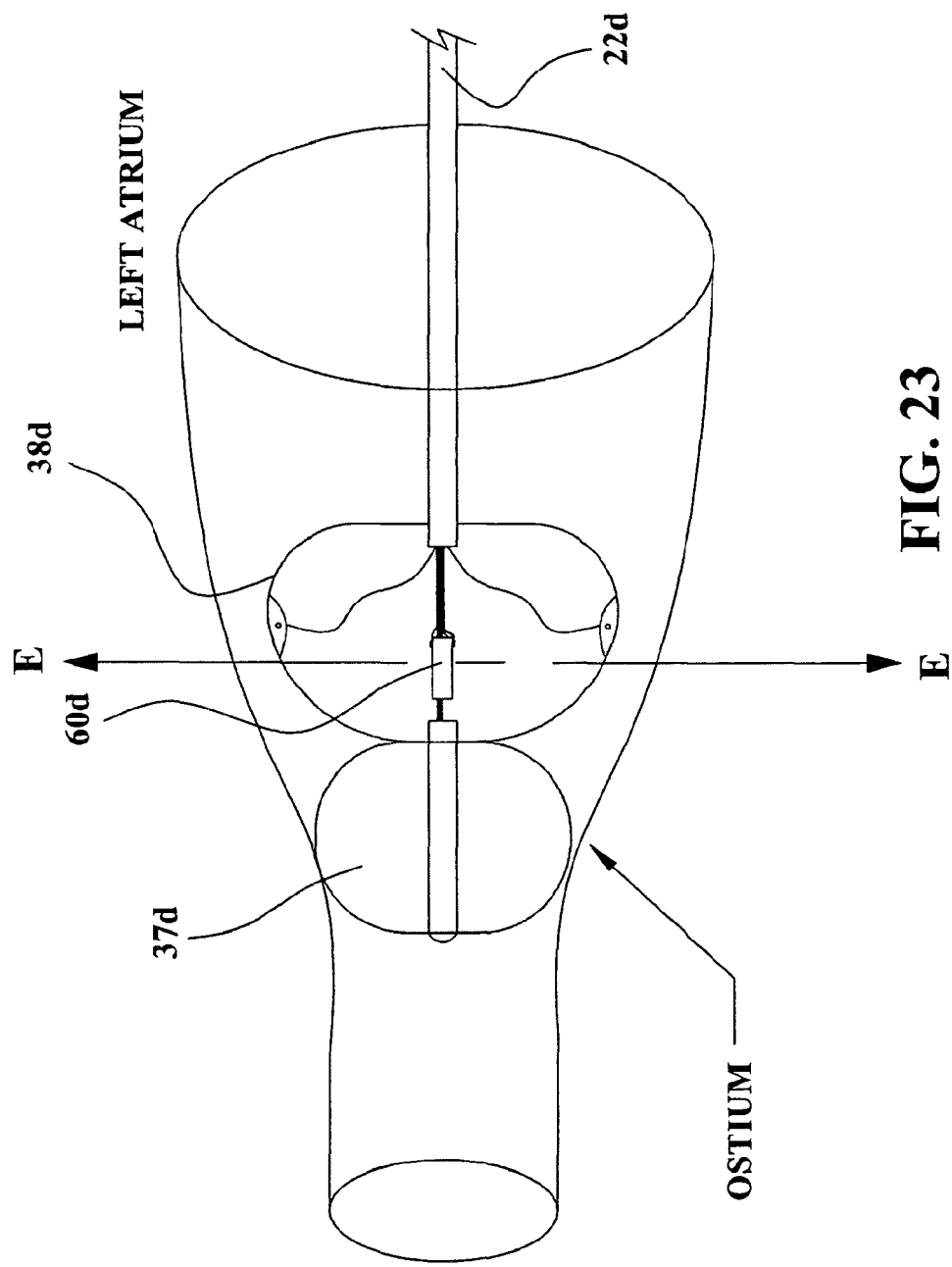
FIG. 23 is a cross-sectional view illustrating the catheter of FIGS. 17 and 18 in use in a pulmonary vein.
Figure 24:
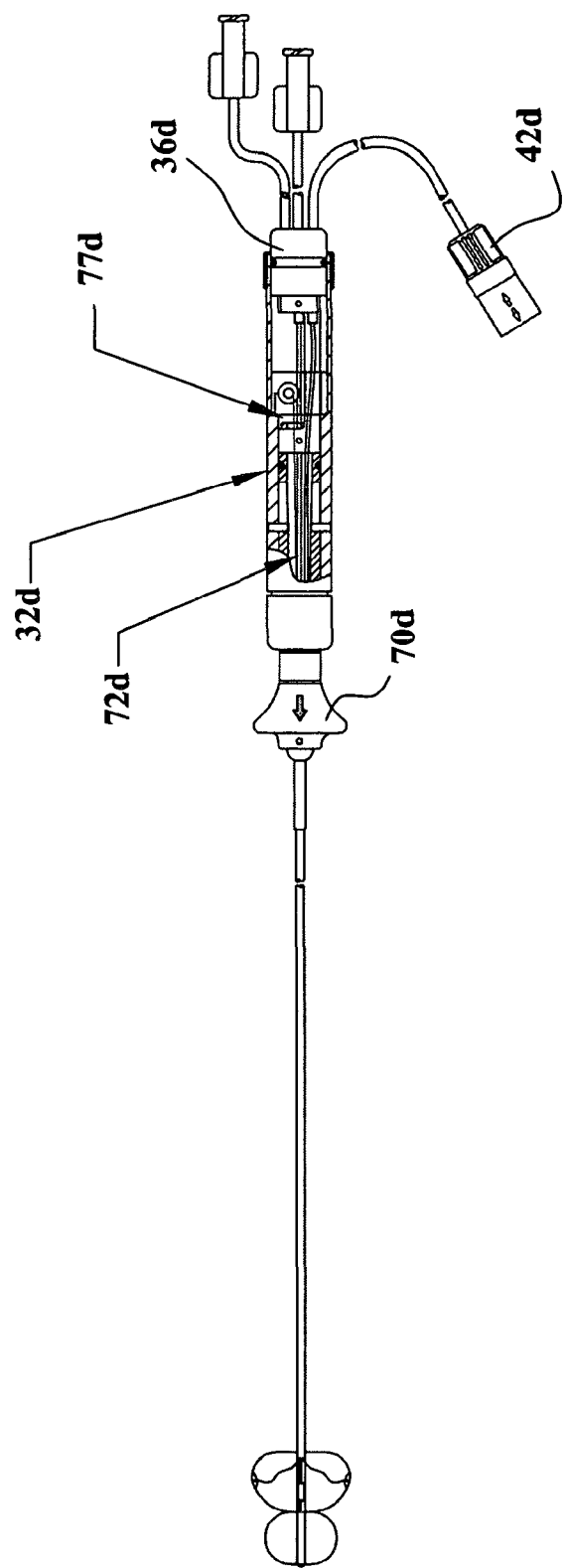
FIG. 24 illustrates the steering mechanism of the catheter of FIGS. 17 and 18.

FIGS. 22 and 23 illustrate how the catheter system 20d is used. The primary difference between the operation of the catheter systems 20 and 20d is that mapping is not provided in the catheter system 20d because there is no distal ring, and therefore no ring electrodes. First, a transseptal sheath 88d is provided to deliver the shaft 22d and the balloon 37d to the desired location (e.g., the left atrium) in the heart. The shaft 22d is slid into the hollow lumen of the sheath 88d, and the sheath 88d can slide forward and backward along the longitudinal axis of the shaft 22d.

To introduce and deploy the distal tip section 24d within the heart, the physician uses a conventional introducer to establish access to a selected artery or vein. With the balloons 37d and 38d deflated, the physician introduces the shaft 22d and the transseptal sheath 88d and progressively advances the sheath 88d through the access vein or artery into the desired atrium, such as the left atrium via standard transseptal as shown in FIG. 22. The physician observes the progress of the sheath 88d using fluoroscopic or ultrasound imaging. The sheath 88d can include a radio-opaque compound, such as barium, for this purpose. Alternatively, radio-opaque markers can be placed at the distal end of the sheath 88d.

The shaft 22d and the sheath 88d can be maneuvered to the left atrium by the steering mechanism 70d. See FIG. 23. Once located in the left atrium, the physician slides the sheath 88d back to expose the balloons 37d and 38d. The balloon 37d is then maneuvered and then expanded into contact with the selected annulus (e.g., the ostium) with the aid of fluoroscopy.

Once the positioning operation has been completed and the desired position of the balloon 38d has been confirmed, the physician can then inflate the balloon 38d using inflation media. The balloon 38d can be manufactured using known techniques to a predetermined diameter so that its diameter at its maximum expansion will be greater than the diameter of the other balloon 37d and the annulus or vessel where the ablation is to take place. This allows the smaller-diameter balloon 37d to snugly contact and anchor a smaller-diameter vessel (e.g., the ostium in FIG. 23) while ablation is being performed in a larger-diameter vessel. The thermocouple wires 54d can also function to monitor the temperature of the surrounding tissue, and provide temperature information to the ultrasound generator 52d. The physician then controls the ultrasound generator 52d to generate ultrasound energy that is propagated through the wires 63d to the ultrasound transducer 60d that is positioned inside the balloon 38d. The energy radiates in a radial manner from the transducer 60d, propagates through the inflation media (which acts as an energy transmitting medium) inside the balloon 38d, exits the balloon 38d and then reaches the selected tissue (typically in a waveform) to ablate the tissue. See the arrows E in FIG. 23 which illustrate the radiation of the energy from the transducer 60d.

Thus, during the ablation, the balloon 37d functions to anchor the distal tip section 24d inside the PV at the desired location so that the ablation can be performed accurately. In contrast to known catheter systems where the same element is used to anchor and ablate, by providing a separate element (i.e., the balloon 37d) to anchor the distal tip section 24d, the function of the ablation element (i.e., the balloon 38d and transducer 60d) will not be affected by the anchoring device, thereby ensuring that the ablation is performed accurately and effectively.

When the ablation has been completed, the balloon 38d is deflated and the distal tip section 24d withdrawn from the heart.

FIGS. 25-30 illustrate modifications made to the catheter system 20d of FIGS. 17-24 to allow contrast medium to be introduced while the catheter is located within the vessel ostium and the balloon 38d inflated. The catheter system 20e in FIGS. 25-30 essentially provides an additional tubing and lumen to facilitate the injection of the contrast medium. The catheter system 20d in FIGS. 17-24 did not provide an additional lumen, so the contrast medium for vessel geometry and catheter location could not be readily verified. Hence, the catheter system 20e makes it easier to verify vessel geometry and catheter location since the blood flow from within the vessel will not wash out when the contrast medium is injected due to balloon inflation.

Since the catheter system 20e merely includes modifications to the catheter system 20d, the descriptions relating to the same elements and their functions will not be repeated herein. Instead, the same numerals used to designate elements in FIGS. 17-24 will be used to designate the same elements in FIGS. 25-30, except that an "e" will be added to the designations in FIGS. 25-30.

Figure 25:
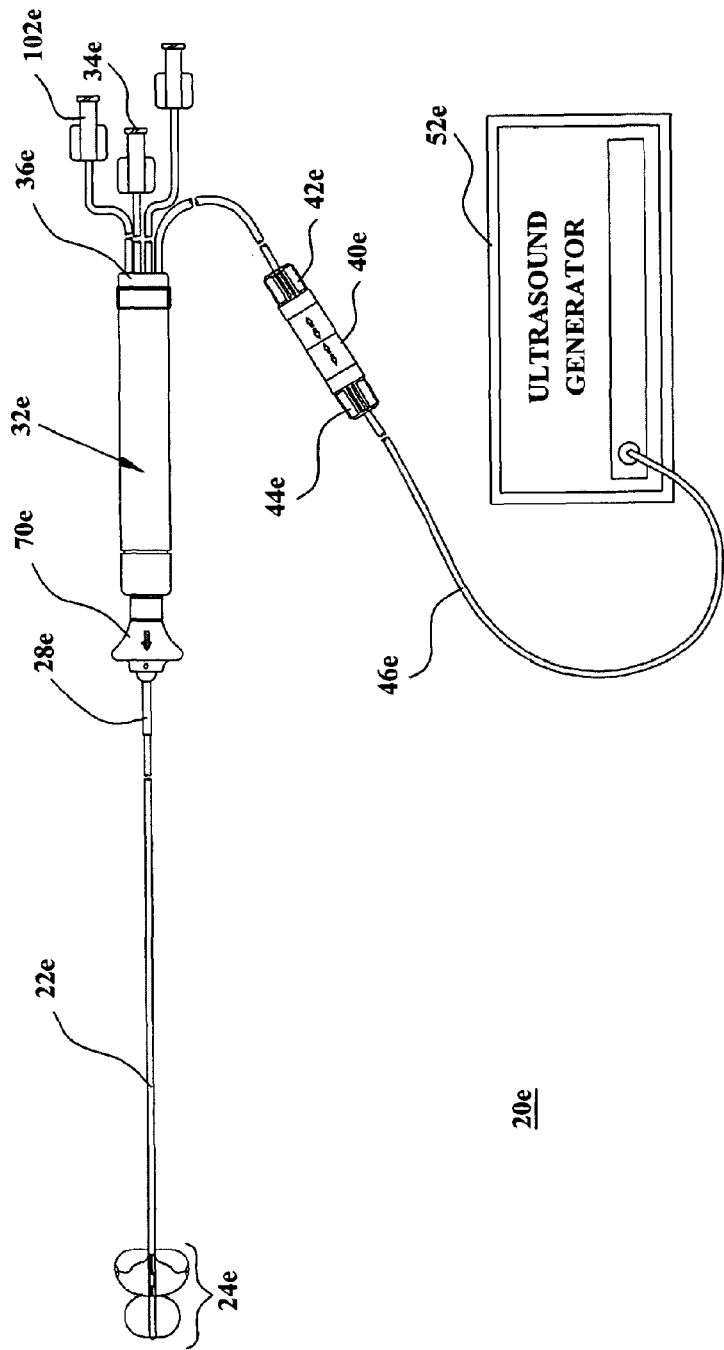
FIG. 25 illustrates an ablation system according to yet a further embodiment of the present invention.
Figure 26:
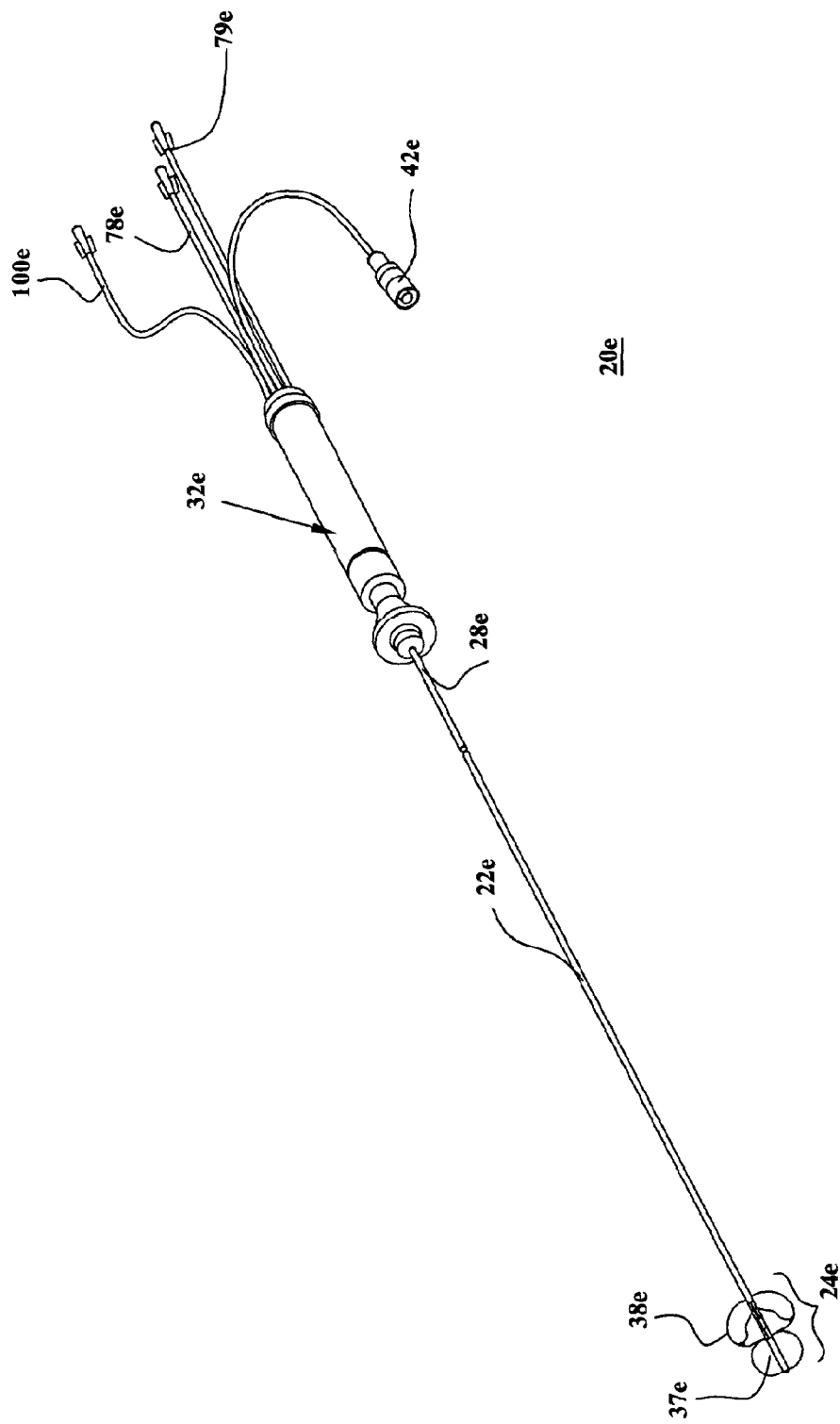
FIG. 26 is a perspective view of the catheter of the system of FIG. 25.
Figure 27:
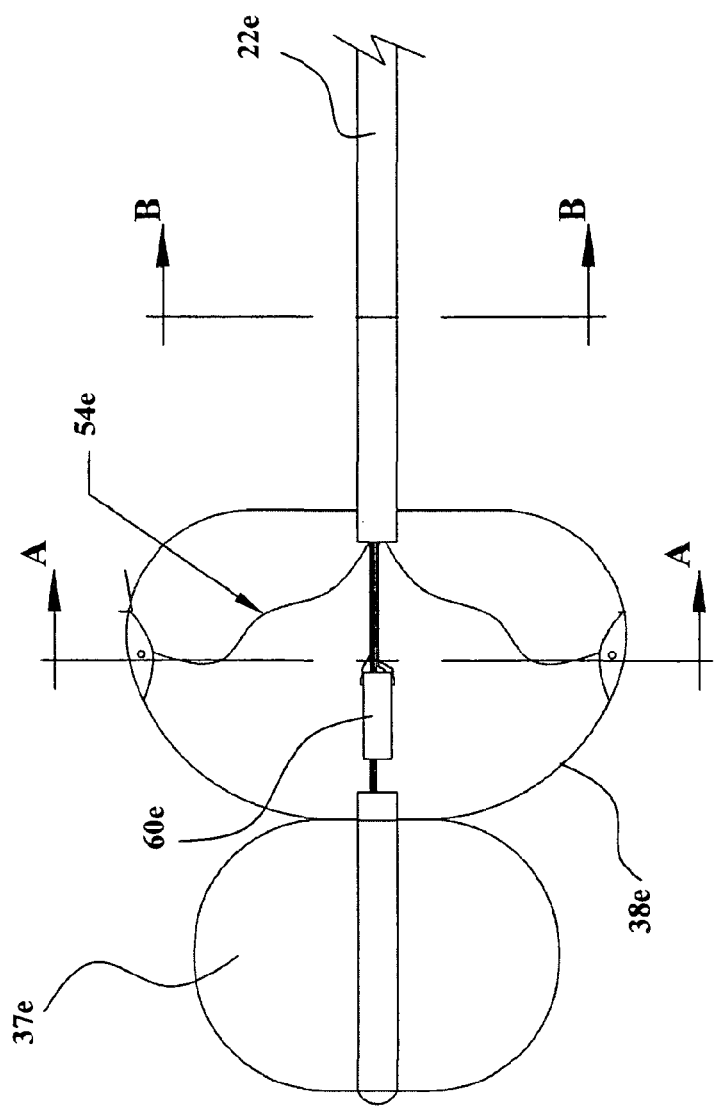
FIG. 27 is an enlarged view of the distal tip section of the catheter of FIGS. 25 and 26.
Figure 28:
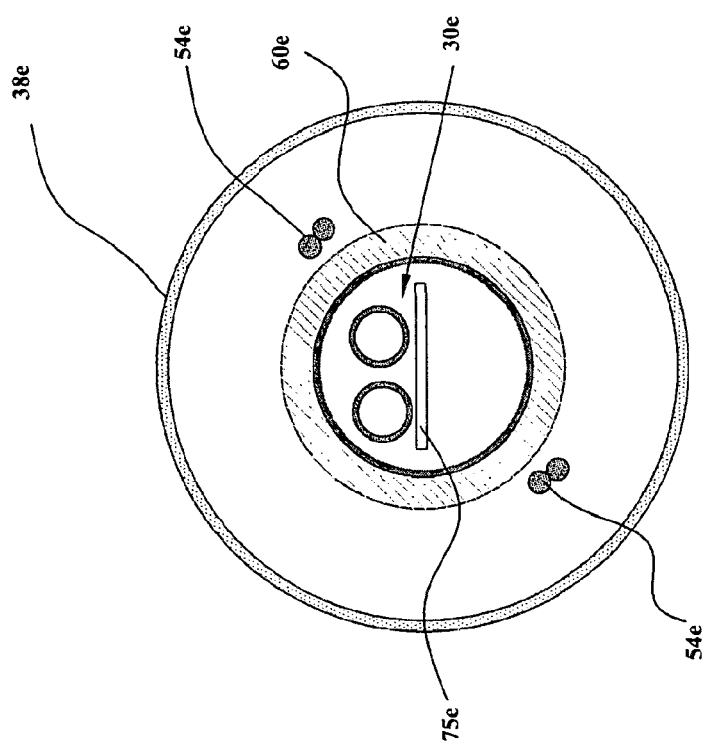
FIG. 28 is a cross-sectional view of the distal tip section of FIG. 27 taken along lines A-A thereof.
Figure 29:
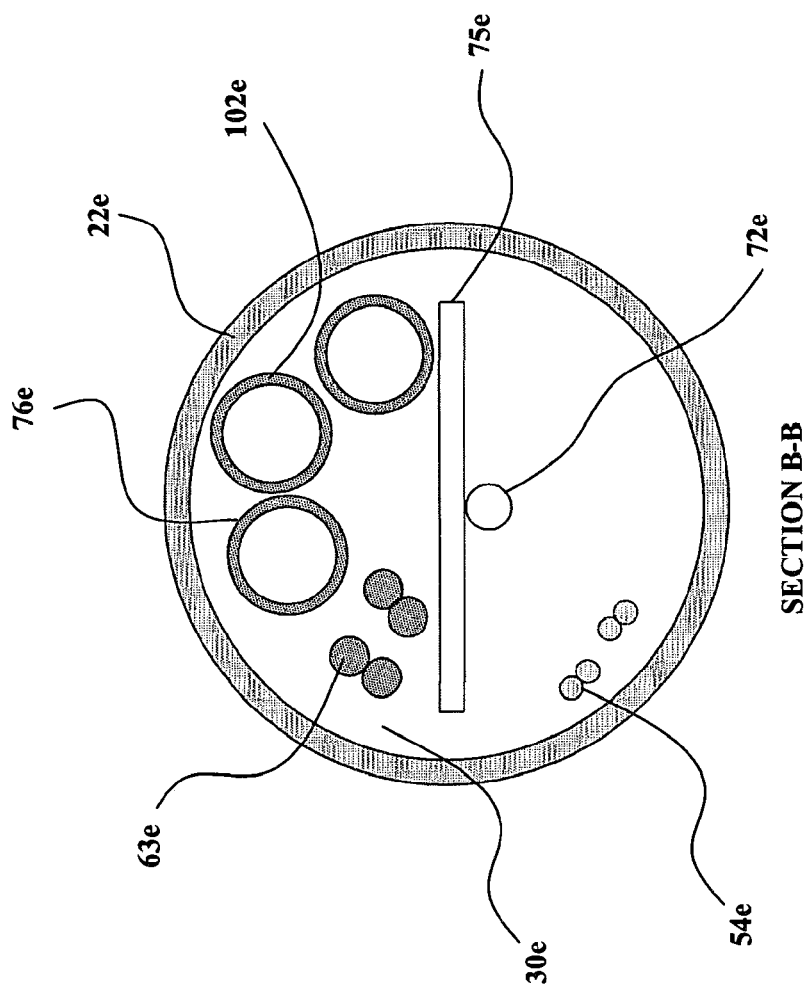
FIG. 29 is a cross-sectional view of the distal tip section of FIG. 27 taken along lines B-B thereof.
Figure 30:
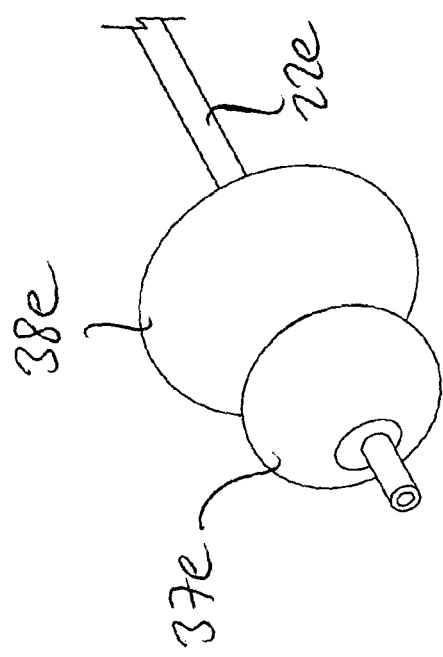
FIG. 30 is an enlarged perspective view of the distal tip section of the catheter of FIGS. 25 and 26.

The catheter system 20e provides an additional tubing 100e that extends from the handle assembly 32e (see FIGS. 25-26). This tubing 100e is connected to a lumen 102e that extends through the shaft 22e, the transducer 60e inside the second balloon 38e, and exits at the distal-most end of the shaft 22e. See FIGS. 27 and 30. The contrast medium can be injected via the tubing 100e and the lumen 102e by a syringe (not shown), and exits the catheter into the blood vessel at the location of the balloon 37e to provide visibility of the location of the balloons 37e and 38e. A guidewire (not shown) can be inserted into this lumen 102e to increase the mobility of the shaft 22e into branches of the main vessel.

In addition, the flat wire 75e extends in the lumen 30e from the distal section of the shaft 22e (not shown in FIGS. 25-30).

Figure 31:
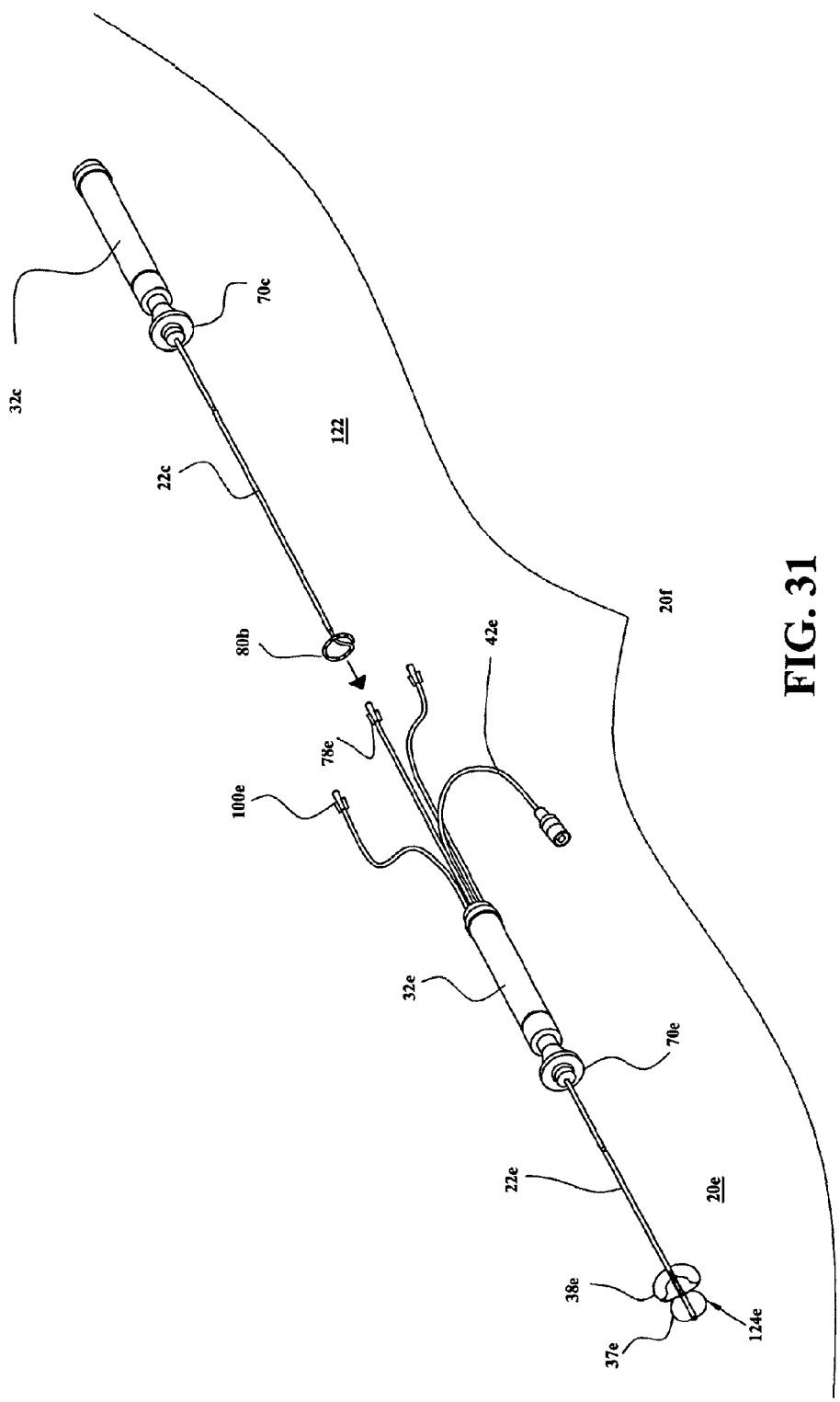
FIG. 31 illustrates a mapping and ablation system according to yet another embodiment of the present invention.
Figure 32:
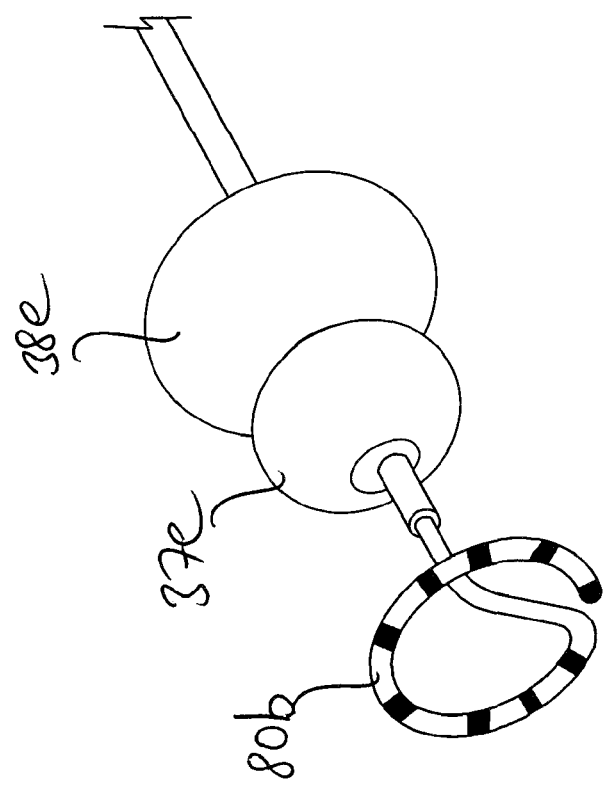
FIG. 32 is an enlarged perspective view of the distal tip section of the catheter of FIG. 31.

FIGS. 31-32 illustrate yet another modification that can be made to the system 20d in FIGS. 17-24. The catheter system 20f in FIGS. 31-32 is comprised of two separate catheters, a first catheter 20e that is identical to the catheter 20e in FIGS. 25-30 above, and a second catheter 122 that is identical to the catheter 122 in FIGS. 15 and 16.

The distal ring 80b and the shaft 22c of the catheter 122 can be inserted through the lumen 102e of the catheter 20e. In this regard, the distal ring 80b can be progressively straightened out and drawn into the lumen 102e of the catheter 20e. Thus, when confined with the catheter 20e, the distal ring 80b assumes the generally linear low profile shape of the catheter 20e. When the distal ring 80b exits the distal-most end 124e of the catheter 20e (see FIG. 32), the distal ring 80b is uncovered and its shape memory (e.g., Nitinol) will cause the distal ring 80b to re-assume its preformed generally circular shape.

The catheter 122 can also be steered so that the diameter of the distal ring 80b can be varied. This can be accomplished by providing a pulling wire (not shown, but can be the same as 72 or 72a), and then pulling the pulling wire. The catheter 20e can also be steered so that the distal end 124e can be deflected.

The following illustrates one example of a possible use of the catheter system 20f. A transseptal sheath (with a dilator in the sheath lumen) is typically inserted into the patient's femoral vein and placed into the right atrium. Using a transseptal (Brockenbrough) needle, a puncture is produced in the fossa ovalis in the septal wall to provide access from the right atrium to the left atrium. The sheath is then brought inside the left atrium, the needle removed, and a guidewire is inserted through the lumen of the dilator to the target pulmonary vein or its branches. The distal opening of the dilator inside the sheath follows the guidewire to the pulmonary vein. When the catheter 20e is used, only the dilator is removed and the lumen 102e of the distal end of the catheter follows the path of the guidewire and into the target PV. Once the catheter 20e is situated in the pulmonary vein ostium, the balloon 38e is inflated until it engages the ostial wall. Contrast media is injected in the lumen 102e to visually verify the location of the transducer 60e with respect to the pulmonary vein anatomy.

For the catheter 20e, the location of the transducer 60e can be verified via contrast medium injection while the distal ring 80e records the PV potentials. This has not been possible with the conventional systems.

For the catheter system 20f, the catheter 122 is inserted through the tubing 100e and the distal ring 80b exits from the lumen 102e. The diameter of the distal ring 80b can be adjusted to fit the different sizes of the pulmonary vein. The electrodes 58b are again used to pick up the PV potentials. Once the potentials (or intracardiac signals) are recorded, the catheter 122 can be removed, and if needed, contrast medium can be injected for locating the transducer. Energy can then be delivered to perform the ablation, as described above.

While the description above refers to particular embodiments of the present invention, it will be understood that many modifications may be made without departing from the spirit thereof. The accompanying claims are intended to cover such modifications as would fall within the true scope and spirit of the present invention.

We claim:

1. A system for sensing electrical events about a selected intrabody annulus region and for treating tissue in the selected annulus region, comprising:
a first catheter and a second catheter;
the first catheter comprising:
a first handle assembly;
a first shaft having a first proximal end coupled to the first handle assembly, and a first distal end, the first shaft extending along a first axis;
a first lumen extending entirely through the first distal end of the first shaft along the first axis;
a second lumen extending entirely through the first distal end of the first shaft along the first axis;
an ablation element provided adjacent the first distal end of the first shaft;
an expandable member adjacent the first distal end; and
wherein the first lumen is adapted to receive the second catheter therethrough;
the second catheter comprising:
a second handle assembly;
a second shaft having a second proximal end coupled to the second handle assembly, and a second distal end, the second shaft of the second catheter extending along a second axis; and
a distal ring provided at the second distal end of the second shaft of the second catheter and oriented substantially perpendicular to the second axis of the second shaft of the second catheter, the distal ring having a plurality of discrete electrodes positioned about the distal ring of the second catheter.

2. The system according to claim 1, wherein the ablation element comprises a transducer.

3. The system according to claim 2, wherein the transducer comprises one of a radiofrequency ablation element or an acoustic ablation element.

4. The system according to claim 1, wherein the distal ring has a first diameter that is less than a second diameter of the fully expanded expandable member.

5. The system according to claim 1, wherein the ablation element is housed inside the expandable member.

6. The system according to claim 5, wherein the expandable member comprises an inflatable balloon.

7. The system according to claim 1, wherein the first handle assembly is configured to deflect the first distal end of the first catheter.

8. The system according to claim 1, wherein the second handle assembly is configured to deflect the second distal end of the second catheter.

9. The system according to claim 1, wherein the second handle assembly is configured to change a diameter of the distal ring.

10. The system according to claim 1, further comprising an energy source coupled to the ablation element.

11. A system for sensing electrical events about a selected annulus region for treating internal body tissue in the selected annulus region, comprising:
a first catheter and a second catheter;
the first catheter comprising:
a first handle assembly;
a first shaft having a first proximal end coupled to the first handle assembly, and a first distal end, the first shaft extending along a first axis;
a first lumen extending through the first shaft along the first axis to a first opening at the first distal end;
a second lumen extending through the first shaft along the first axis to a second opening at the first distal end;
an expandable member adjacent the first distal end; and
an ablation element positioned within the expandable member, wherein the first lumen is adapted to receive the second catheter therethrough, and wherein only the first and second openings are distal of the expandable member along the first shaft;

the second catheter comprising:

a second handle assembly;

a second shaft having a second proximal end coupled to the second handle assembly, and a second distal end, the second shaft of the second catheter extending along a second axis; and a distal ring provided at the second distal end of the second shaft of the second catheter and oriented substantially perpendicular to the second axis of the second shaft of the second catheter, the distal ring having a plurality of electrodes positioned in spaced-apart manner about the distal ring of the second catheter.

12. The system according to claim 11, wherein the distal ring has a first diameter that is less than a second diameter of the expandable member when fully expanded.

13. A system for sensing electrical events about a selected annulus region of the heart and for treating tissue in the selected annulus region, comprising:

a first catheter and a second catheter;

the first catheter comprising:

a first handle assembly;

a first shaft having a first proximal end coupled to the first handle assembly, and a first distal end, the first shaft extending along a first axis;

a first lumen extending to a first opening at the first distal end of the first shaft along the first axis;

a second lumen extending to a second opening at the first distal end of the first shaft along the first axis;

an expandable member positioned on the first shaft immediately proximal of the first and second openings; and an ablation element provided within the expandable member, wherein the first lumen is adapted to receive the second catheter therethrough;

the second catheter comprising:

a second handle assembly;

a second shaft having a second proximal end coupled to the second handle assembly, and a second distal end, the second shaft of the second catheter extending along a second axis; and a distal ring provided at the second distal end of the second shaft of the second catheter and oriented substantially perpendicular to the second axis of the second shaft of the second catheter, the distal ring having a plurality of electrodes positioned in spaced-apart manner about the distal ring of the second catheter.

* * * * *